(12) United States Patent
Komatsu et al.

(10) Patent No.: US 11,525,037 B2
(45) Date of Patent: Dec. 13, 2022

(54) TETRACARBOXYLIC DIANHYDRIDE, POLYIMIDE PRECURSOR RESIN AND SOLUTION THEREOF, AND POLYIMIDE AND SOLUTION THEREOF

(71) Applicant: ENEOS CORPORATION, Tokyo (JP)

(72) Inventors: Shinichi Komatsu, Tokyo (JP); Asako Kyobu, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 211 days.

(21) Appl. No.: 16/608,742

(22) PCT Filed: Apr. 23, 2018

(86) PCT No.: PCT/JP2018/016434
§ 371 (c)(1),
(2) Date: Oct. 25, 2019

(87) PCT Pub. No.: WO2018/199014
PCT Pub. Date: Nov. 1, 2018

(65) Prior Publication Data
US 2020/0239636 A1   Jul. 30, 2020

(30) Foreign Application Priority Data

Apr. 28, 2017  (JP) .............................. JP2017-089810

(51) Int. Cl.
*C08G 73/10* (2006.01)
*C08L 79/08* (2006.01)
*C07D 493/10* (2006.01)

(52) U.S. Cl.
CPC ....... *C08G 73/1078* (2013.01); *C07D 493/10* (2013.01); *C08G 73/1039* (2013.01); *C08L 79/08* (2013.01)

(58) Field of Classification Search
None
See application file for complete search history.

(56) References Cited

U.S. PATENT DOCUMENTS

2012/0310013 A1  12/2012  Komatsu et al.
2013/0079490 A1   3/2013  Matsumoto et al.
(Continued)

FOREIGN PATENT DOCUMENTS

JP  2014-218460 A  11/2014
JP  2015-137231 A   7/2015
(Continued)

OTHER PUBLICATIONS

Jul. 6, 2020 Office Action issued in Japanese Patent Application No. 2017-089810.
(Continued)

*Primary Examiner* — Rachel Kahn
(74) *Attorney, Agent, or Firm* — Oliff PLC

(57) ABSTRACT

A tetracarboxylic dianhydride represented by the following general formula (1):

[Chem. 1]

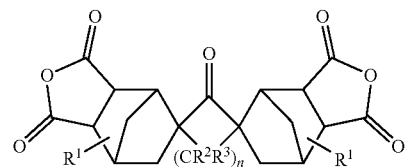

[in the formula (1), $R^1$, $R^2$, and $R^3$ each independently represent a hydrogen atom and the like, and n represents an integer of 0 to 12], wherein a ratio of a summed amount of a specific stereoisomer (A) and a specific stereoisomer (B) is 50% by mole or more relative to a total amount of stereoisomers based on three-dimensional configurations of two norbornane rings in the general formula (1), and a (Continued)

content ratio of the stereoisomer (A) is 30% by mole or more relative to the total amount of the stereoisomers.

5 Claims, 7 Drawing Sheets

(56) References Cited

U.S. PATENT DOCUMENTS

| | | |
|---|---|---|
| 2015/0218317 A1 | 8/2015 | Komatsu et al. |
| 2015/0307662 A1 | 10/2015 | Oka et al. |
| 2015/0343432 A1 | 12/2015 | Komatsu et al. |
| 2016/0102044 A1 | 4/2016 | Watanabe et al. |
| 2016/0297995 A1* | 10/2016 | Oka .................. C09D 179/08 |
| 2016/0347699 A1 | 12/2016 | Fujishiro et al. |
| 2017/0044322 A1 | 2/2017 | Noguchi et al. |
| 2017/0197948 A1 | 7/2017 | Fujishiro et al. |
| 2018/0237638 A1 | 8/2018 | Matsuo et al. |

FOREIGN PATENT DOCUMENTS

| | | | |
|---|---|---|---|
| JP | 2015-137235 A | 7/2015 | |
| JP | 2015-218160 A | 12/2015 | |
| JP | 2016-132686 A | 7/2016 | |
| TW | 201418328 A | 5/2014 | |
| WO | 2011/099517 A1 | 8/2011 | |
| WO | 2011/099518 A1 | 8/2011 | |
| WO | 2014/034760 A1 | 3/2014 | |
| WO | 2014/046064 A1 | 3/2014 | |
| WO | 2014/050788 A1 | 4/2014 | |
| WO | 2014/050810 A1 | 4/2014 | |
| WO | WO-2015053312 A1 * | 4/2015 | ......... C08G 73/1078 |
| WO | 2015/163314 A1 | 10/2015 | |
| WO | 2015/178261 A1 | 11/2015 | |
| WO | 2016/084777 A1 | 6/2016 | |
| WO | 2017/030019 A1 | 2/2017 | |

OTHER PUBLICATIONS

Kimura et al., "Colorless and thermally stable polymer—An alicyclic polyimide with cyclopentanone bis-spironorbornane structure," Japanese Journal of Polymer Science and Technology, 2011, vol. 68, No. 3, pp. 127-131.
May 22, 2018 International Search Report issued in International Patent Application No. PCT/JP2018/016434.
Oct. 29, 2019 International Preliminary Report on Patentability issued in International Patent Application No. PCT/JP2018/016434.
Jun. 2, 2021 Office Action issued in Chinese Patent Application No. 201880006933.8.
Transaltion of Kimura et al., "Colorless and thermally stable polymer—An alicyclic polyimide with cyclopentanone bis-spironorbornane structure," Japanese Journal of Polymer Science and Technology, 2011, vol. 68, No. 3, pp. 127-131.
Sep. 15, 2021 Office Action issued in Taiwanese Patent Application No. 107114427.
Mar. 18, 2022 Office Action issued in Taiwanese Patent Application No. 107114427.

* cited by examiner

TETRACARBOXYLIC DIANHYDRIDE, POLYIMIDE PRECURSOR RESIN AND SOLUTION THEREOF, AND POLYIMIDE AND SOLUTION THEREOF

TECHNICAL FIELD

The present invention relates to a tetracarboxylic dianhydride, a polyimide precursor resin and a solution thereof, and a polyimide and a solution thereof.

BACKGROUND ART

Conventionally, polyimides have attracted attention as a material which has a high heat resistance and which is lightweight and flexible. In the field of such polyimides, polyimides have been required in recent years having heat resistance and sufficient light transmittance usable in glass alternative application and the like as well as having solubility in solvents, and various polyimides have been developed. For example, International Publication No. WO2011/099518 (PTL 1) discloses a polyimide which has a repeating unit expressed by a specific general formula. Such a polyimide has sufficient heat resistance, light transmittance, and solubility. In addition, as a polyimide which has further higher heat resistance than that of the polyimide in PTL 1 described above, International Publication No. WO2014/034760 (PTL 2) also discloses a polyimide which has a repeating unit expressed by a specific general formula. As described above, the polyimides described in PTLs 1 and 2 have sufficient heat resistance and light transmittance as well as solubility in solvents. However, in the field of polyimides, from the viewpoint of further improvement of processability, the advent of polyimides has been required having higher solubility while maintaining heat resistance and transparency to the same extent as the polyimides described in PTLs 1 and 2.

CITATION LIST

Patent Literature

[PTL 1] International Publication No. WO2011/099518
[PTL 2] International Publication No. WO2014/034760

SUMMARY OF INVENTION

Technical Problem

The present invention has been made in view of the problem of the above-described conventional technology, and an object thereof is to provide a tetracarboxylic dianhydride which can be preferably used for producing a polyimide having higher solubility while having sufficiently high levels of heat resistance and transparency. In addition, the present invention aims to provide a polyimide which can have higher solubility while having sufficiently high levels of heat resistance and transparency, and a polyimide solution containing the polyimide. Moreover, the present invention aims to provide a polyimide precursor resin which can be preferably used for producing the polyimide, and a polyimide precursor resin solution containing the polyimide precursor resin.

Solution to Problem

The present inventors have made earnest studies to achieve the above-described objects, and consequently found that the tetracarboxylic dianhydride (which may include six stereoisomers with different three-dimensional configurations of norbornane rings) represented by the following general formula (1) can be preferably used for producing a polyimide having higher solubility while having sufficiently high levels of heat resistance and transparency when the ratio of the summed amount of the following stereoisomers (A) and (B) relative to the total amount of the stereoisomers (stereoisomers based on the three-dimensional configurations of norbornane rings) is 50% by mole or more, and when the content ratio of the following stereoisomer (A) relative to the total amount of the stereoisomers is 30% by mole or more. This finding has led to the completion of the present invention.

Specifically, a tetracarboxylic dianhydride of the present invention is a tetracarboxylic dianhydride represented by the following general formula (1):

[Chem. 1]

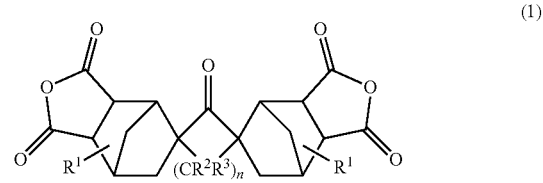

(1)

[in the formula (1), $R^1$, $R^2$, and $R^3$ each independently represent one selected from the group consisting of a hydrogen atom, alkyl groups having 1 to 10 carbon atoms, and a fluorine atom, and n represents an integer of 0 to 12], wherein
a ratio of a summed amount of a stereoisomer (A) represented by the following general formula (2):

[Chem. 2]

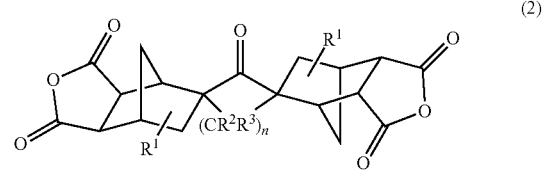

(2)

[$R^1$, $R^2$, $R^3$, and n in the formula (2) have the same definitions as those of $R^1$, $R^2$, $R^3$, and n in the general formula (1), respectively] and a stereoisomer (B) represented by the following general formula (3):

[Chem. 3]

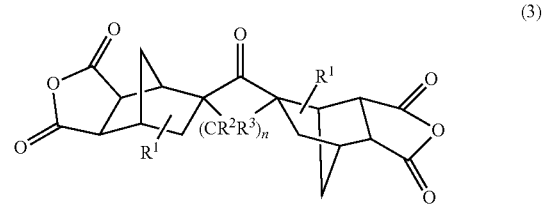

(3)

[$R^1$, $R^2$, $R^3$, and n in the formula (3) have the same definitions as those of $R^1$, $R^2$, $R^3$, and n in the general formula (1), respectively] is 50% by mole or more relative to a total amount of stereoisomers based on three-dimensional configurations of two norbornane rings in the general formula (1), and a content ratio of the stereoisomer (A) is 30% by mole or more relative to the total amount of the stereoisomers.

In addition, a polyimide precursor resin of the present invention is a polyimide precursor resin in which a ratio of a summed amount of a repeating unit (A') represented by the following general formula (4):

[Chem. 4]

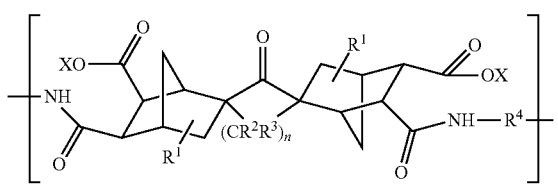
(4)

[in the formula (4), $R^1$, $R^2$, and $R^3$ each independently represent one selected from the group consisting of a hydrogen atom, alkyl groups having 1 to 10 carbon atoms, and a fluorine atom, n represents an integer of 0 to 12, $R^4$ represents an arylene group having 6 to 50 carbon atoms, and X each independently represent one selected from the group consisting of a hydrogen atom, alkyl groups having 1 to 6 carbon atoms, and alkyl silyl groups having 3 to 9 carbon atoms] and a repeating unit (B') represented by the following general formula (5):

[Chem. 5]

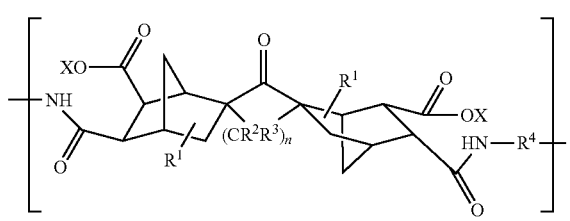
(5)

[$R^1$, $R^2$, $R^3$, $R^4$, n, and X in the formula (5) have the same definitions as those of $R^1$, $R^2$, $R^3$, $R^4$, n, and X in the general formula (4), respectively] is 50% by mole or more relative to a total amount of all repeating units, and a content ratio of the repeating unit (A') is 30% by mole or more relative to the total amount of all the repeating units.

In addition, a polyimide of the present invention is a polyimide in which a ratio of a summed amount of a repeating unit (A) represented by the following general formula (6):

[Chem. 6]

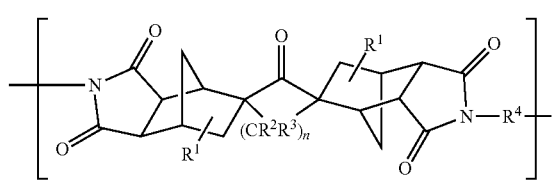
(6)

[in the formula (6), $R^1$, $R^2$, and $R^3$ each independently represent one selected from the group consisting of a hydrogen atom, alkyl groups having 1 to 10 carbon atoms, and a fluorine atom, n represents an integer of 0 to 12, and $R^4$ represents an arylene group having 6 to 50 carbon atoms] and a repeating unit (B) represented by the following general formula (7):

[Chem. 7]

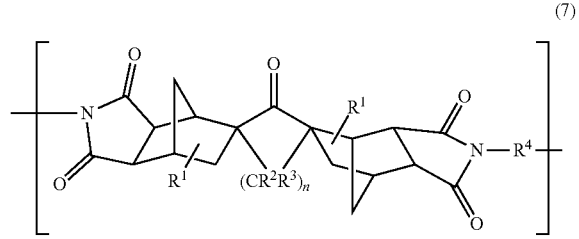
(7)

[$R^1$, $R^2$, $R^3$, $R^4$, and n in the formula (7) have the same definitions as those of $R^1$, $R^2$, $R^3$, $R^4$, and n in the general formula (6), respectively] is 50% by mole or more relative to a total amount of all repeating units, and a content ratio of the repeating unit (A) is 30% by mole or more relative to the total amount of all the repeating units.

Moreover, a polyimide solution of the present invention comprises the polyimide of the present invention and an organic solvent. In addition, a polyimide precursor resin solution of the present invention comprises the polyimide precursor resin of the present invention and an organic solvent. A resin solution (varnish) such as the above polyimide solution and polyimide precursor resin solution (for example, a polyamic acid solution) makes it possible to efficiently produce various forms of polyimides. Note that the above polyimide solution and polyimide precursor resin solution can be preferably used for preparing a polyimide as a resin solution in the form of a mixture liquid obtained by mixing them.

Advantageous Effects of Invention

The present invention makes it possible to provide a tetracarboxylic dianhydride which can be preferably used for producing a polyimide having higher solubility while having sufficiently high levels of heat resistance and transparency. In addition, the present invention makes it possible to provide a polyimide which can have higher solubility while having sufficiently high levels of heat resistance and transparency, and a polyimide solution containing the polyimide. Moreover, the present invention makes it possible to provide a polyimide precursor resin which can be preferably used for producing the polyimide, and a polyimide precursor resin solution containing the polyimide precursor resin.

DESCRIPTION OF EMBODIMENTS

Figure 1:
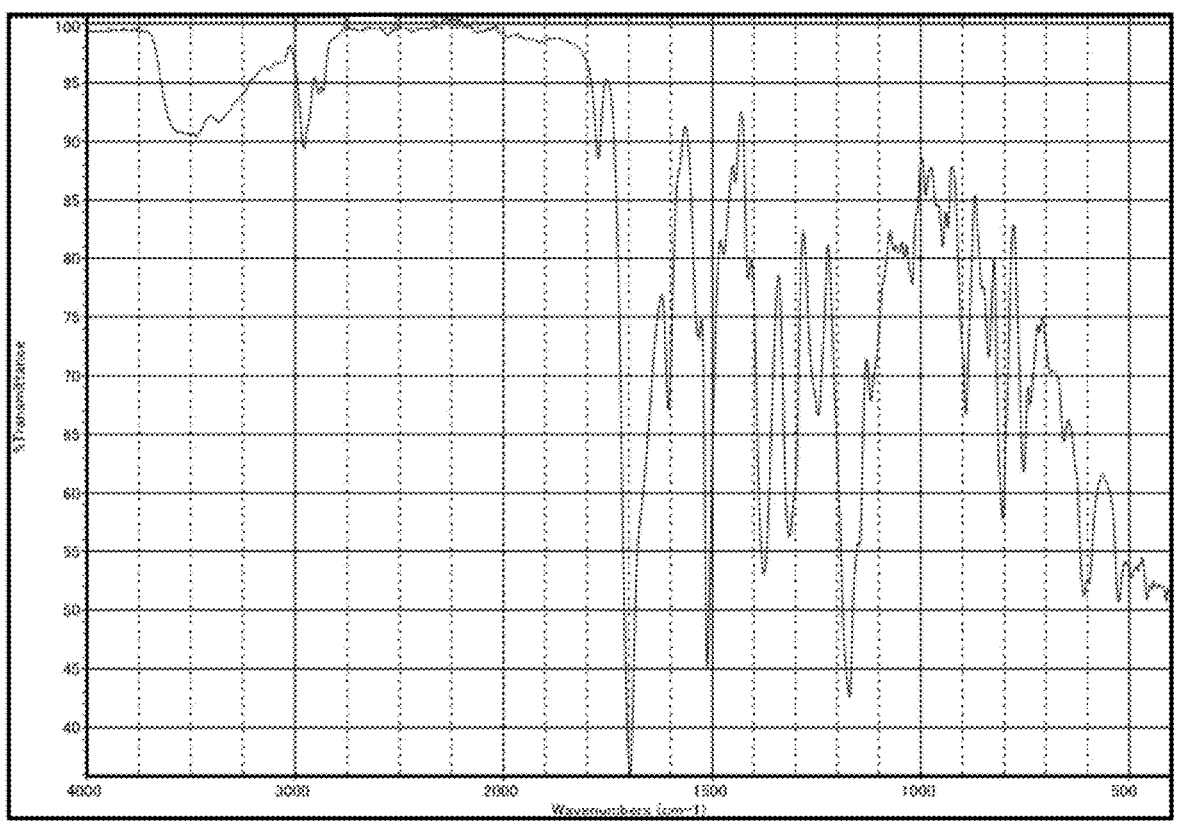
FIG. 1 is a graph showing an IR spectrum of a tetracarboxylic acid tetramethyl ester (intermediate) obtained in Example 1.

Hereinafter, the present invention is described in detail with reference to its preferred embodiments.

[Tetracarboxylic Dianhydride]

A tetracarboxylic dianhydride of the present invention is a tetracarboxylic dianhydride represented by the general formula (1), wherein a ratio of a summed amount of a stereoisomer (A) represented by the general formula (2) and a stereoisomer (B) represented by the general formula (3) is 50% by mole or more relative to a total amount of stereoisomers based on three-dimensional configurations of two norbornane rings in the general formula (1), and a content ratio of the stereoisomer (A) is 30% by mole or more relative to the total amount of the stereoisomers.

$R^1$, $R^2$, and $R^3$ in the general formula (1) are each independently one selected from the group consisting of a hydrogen atom, alkyl groups having 1 to 10 carbon atoms, and a fluorine atom, and n is an integer of 0 to 12. Note that $R^1$, $R^2$, $R^3$, and n in the general formulae (2) and (3) have the same definitions as those of $R^1$, $R^2$, $R^3$, and n in the general formula (1), respectively.

The alkyl group which can be selected as any one of $R^1$, $R^2$, and $R^3$ in the formula is an alkyl group having 1 to 10 carbon atoms. If the number of the carbon atoms exceeds 10, the glass transition temperature is lowered, so that a sufficiently high heat resistance cannot be achieved. In addition, the number of carbon atoms of the alkyl group which can be selected as any one of $R^1$, $R^2$, and $R^3$ is preferably 1 to 6, more preferably 1 to 5, further preferably 1 to 4, and particularly preferably 1 to 3, from the viewpoint that the purification is easier. In addition, the alkyl group which can be selected as any one of $R^1$, $R^2$, and $R^3$ may be linear or branched. Moreover, the alkyl group is more preferably a methyl group or an ethyl group from the viewpoint of ease of purification.

$R^1$, $R^2$, and $R^3$ in the formula are each independently more preferably a hydrogen atom or an alkyl group having 1 to 10 carbon atoms from the viewpoint that a higher heat resistance can be obtained in the production of a polyimide. Especially, $R^1$, $R^2$, and $R^3$ are each independently more preferably a hydrogen atom, a methyl group, an ethyl group, an n-propyl group, or an isopropyl group, and particularly preferably a hydrogen atom or a methyl group, from the viewpoints that the raw materials are readily available and that the purification is easier. In addition, the multiple $R^1$s, $R^2$s, and $R^3$s in each of the formulae are particularly preferably the same, from the viewpoints of ease of purification and the like.

In addition, n in the formulae represents an integer of 0 to 12. If the value of n exceeds the upper limit, the purification is difficult. In addition, an upper limit value of the numeric value range of n in the general formula (1) is more preferably 5, and particularly preferably 3, from the viewpoint that the purification is easier. Meanwhile, a lower limit value of the numeric value range of n in the general formula (1) is more preferably 1, and particularly preferably 2, from the viewpoint of the stability of a raw material compound. Accordingly, n in the general formula (1) is particularly preferably an integer of 2 or 3.

In addition, the tetracarboxylic dianhydride represented by the general formula (1) can contain six stereoisomers based on the three-dimensional configurations of two norbornane rings in the general formula (1). The six stereoisomers mentioned here are the stereoisomer (A) represented by the general formula (2) (trans-exo-endo isomer); the stereoisomer (B) represented by the general formula (3) (cis-exo-endo isomer); and four isomers represented by the following general formulae (I) to (IV):

[Chem. 8]

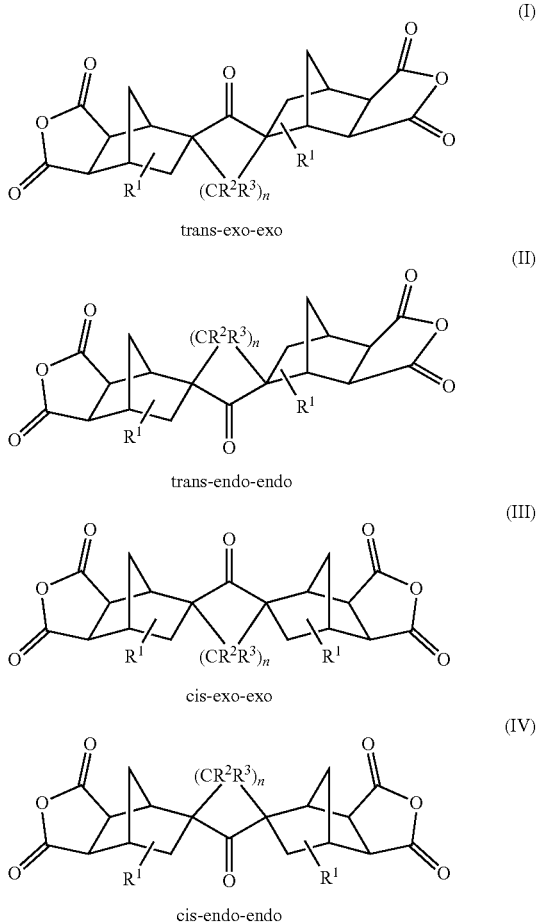

[$R^1$, $R^2$, $R^3$, and n in the formulae have the same definitions as those of $R^1$, $R^2$, $R^3$, and n in the general formula (1), respectively] (trans-exo-exo isomer: a stereoisomer (C) represented by the general formula (I), trans-endo-endo isomer: a stereoisomer (D) represented by the general formula (II), cis-exo-exo isomer: a stereoisomer (E) represented by the general formula (III), cis-endo-endo isomer: a stereoisomer (F) represented by the general formula (IV)).

As the tetracarboxylic dianhydride of the present invention, the ratio (ratio based on mole) of the summed amount of the stereoisomer (A) represented by the general formula (2) and the stereoisomer (B) represented by the following general formula (3) needs to be 50% by mole or more relative to the total amount of the stereoisomers (summed amount of all stereoisomers contained in the tetracarboxylic dianhydride). If the ratio of the summed amount of the stereoisomers (A) and (B) is less than the lower limit, the solubility of the obtained polyimide in a solvent decreases in the case of using the tetracarboxylic dianhydride as a raw material of a polyimide (monomer). In addition, the ratio of the summed amount of the stereoisomers (A) and (B) is more preferably 50 to 100% by mole, further preferably 60 to 98% by mole, particularly preferably 70 to 95% by mole, and most preferably 80 to 90% by mole. If the ratio of the summed amount of the stereoisomers (A) and (B) is in the above range, the polyimide tends to have higher solubility while having sufficiently high levels of heat resistance and transparency.

In the tetracarboxylic dianhydride of the present invention, the content ratio of the stereoisomer (A) represented by the general formula (2) (content ratio based on mole of the trans-exo-endo isomer) needs to be 30% by mole or more relative to the total amount of the stereoisomers (summed amount of all stereoisomers contained in the tetracarboxylic dianhydride). If the content ratio of the stereoisomer (A) is less than the lower limit, the solubility of the obtained polyimide in a solvent decreases in the case of using the tetracarboxylic dianhydride as a raw material of a polyimide (monomer). In addition, the content ratio of the stereoisomer (A) is more preferably 30 to 99% by mole, further preferably 40 to 90% by mole, particularly preferably 50 to 85% by mole, and most preferably 60 to 80% by mole. If the content ratio of the stereoisomer (A) is in the above range, the polyimide tends to have higher solubility while having sufficiently high levels of heat resistance and transparency.

In the tetracarboxylic dianhydride of the present invention, the content ratio of the stereoisomer (B) represented by the general formula (3) (content ratio based on mole of the cis-exo-endo isomer) is more preferably 1 to 70% by mole, further preferably 10 to 60% by mole, particularly preferably 10 to 50% by mole, and most preferably 10 to 40% by mole relative to the total amount of the stereoisomers (summed amount of all stereoisomers contained in the tetracarboxylic dianhydride). If the content ratio of the stereoisomer (B) is in the above range, the polyimide tends to have higher solubility while having sufficiently high levels of heat resistance and transparency.

In addition, in the tetracarboxylic dianhydride of the present invention, the ratio (ratio based on mole) of the summed amount of the stereoisomer (D) represented by the general formula (II) and the stereoisomer (F) represented by the general formula (IV) is preferably 50% by mole or less, more preferably 0 to 40% by mole, further preferably 0 to 30% by mole, and particularly preferably 0 to 20% by mole relative to the total amount of the stereoisomers (summed amount of all stereoisomers contained in the tetracarboxylic dianhydride). If the ratio of the summed amount of the stereoisomers (D) and (F) exceeds the upper limit, the solubility of the obtained polyimide in a solvent tends to decrease.

Moreover, in the tetracarboxylic dianhydride of the present invention, the ratio (ratio based on mole) of the summed amount of the stereoisomer (C) represented by the general formula (I) and the stereoisomer (E) represented by the general formula (III) is preferably 10% by mole or less, more preferably 0 to 5% by mole, further preferably 0 to 3% by mole, particularly preferably 0 to 1.5% by mole, and most preferably 0 to 1% by mole relative to the total amount of the stereoisomers (summed amount of all stereoisomers contained in the tetracarboxylic dianhydride). If the ratio of the summed amount of the stereoisomers (C) and (E) exceeds the upper limit, the heat resistance tends to decrease.

In addition, as the content ratio of each isomer in the tetracarboxylic dianhydride, it is possible to employ a value determined as follows (value determined by gas chromatography measurement (GC measurement and GC-MS measurement)). Specifically, first, at least 1 µL of a dimethylacetamide solution (DMAc solution), containing the tetracarboxylic dianhydride to be analyzed as a measurement sample at a ratio of 0.1% by mass, is prepared. A gas chromatograph mass spectrometer (manufactured by Agilent under the trade name of "7890A") is used as a measuring apparatus. Helium is used as a mobile phase gas (carrier gas). RESTEX Rtx-5 Amine (30 m) is used as a stationary phase (column). The trade name "5975C VL MSD" manufactured by Agilent is used as an MS detector. G4513A manufactured by Agilent is used as an injector. The DMAc solution being the measurement sample in an amount of 1 µL is injected with the injector. The flow rate of the helium being a carrier gas is set to 10 mL/min (constant). The temperature conditions is set to the conditions that, after retaining at 50° C. (initial temperature) for 1 minute, the temperature is raised from 50° C. to 300° C. with a rate of temperature rise of 10° C./min, and is retained at 300° C. for 25 minutes. In this way, GC measurement and GC-MS measurement are carried out, and thereby the chromatogram (separation image) of the measurement sample is determined. After that, the area of each of the peaks in the chromatogram is determined, and the content ratio of the isomer derived from each peak is calculated based on the ratio of the area of each peak relative to the sum of areas (total area). Thus, the content ratio of each isomer can be determined. As described above, it is possible to determine the area ratio of each peak in the chromatogram as the content ratio of the isomer derived from that peak (area normalization method). In the chromatogram, the area ratio of the peak based on each isomer can be determined directly with the measuring apparatus.

Note that, regarding the chromatogram determined as described above, the peaks of the six stereoisomers basically appear during a retention time of about 31 minutes to 34 minutes in the case where the tetracarboxylic dianhydride is norbornane-2-spiro-α-cyclopentanone-α'-spiro-2"-norbornane-5,5",6,6'-tetracarboxylic dianhydride. The peak at a retention time of around 31.4 minutes (31.3 minutes to 31.6 minutes) is a peak derived from the trans-exo-exo isomer and the cis-exo-exo isomer, the peak at a retention time of around 31.8 minutes (31.7 minutes to 31.9 minutes) is a peak derived from the cis-exo-endo isomer (the stereoisomer (B)), the peak at a retention time of around 32.4 minutes (32.1 minutes to 32.6 minutes) is a peak derived from the trans-exo-endo isomer (the stereoisomer (A)), and the peak at a retention time of around 33.0 minutes (32.7 minutes to 33.3 minutes) is a peak derived from the trans-endo-endo isomer and the cis-endo-endo isomer. Note that, although there is a slight deviation depending on the column lot, peaks appear generally at the positions of the above retention times.

The tetracarboxylic dianhydride of the present invention can be preferably used as a monomer for producing a polyimide (particularly preferable as a monomer (tetracarboxylic dianhydride) for producing the polyimide of the present invention described later). In addition, in the case of using the tetracarboxylic dianhydride of the present invention as a monomer for producing the polyimide, the tetracarboxylic dianhydride can be used by mixing with a different tetracarboxylic dianhydride. Examples of the different tetracarboxylic dianhydride appropriately usable include known tetracarboxylic dianhydrides which can be used in the production of a polyimide (for example, the compounds listed in paragraph [0171] of WO 2014/034760 A (aliphatic or alicyclic tetracarboxylic dianhydrides and aromatic tetracarboxylic dianhydrides) and the like).

A preferable method for producing the tetracarboxylic dianhydride of the present invention is not particularly limited, and it is possible to employ, for example, a method described below (method including a first ester compound formation step, a second ester compound production step, and a tetracarboxylic dianhydride production step: hereinafter simply referred to as the "production method (A)" for convenience). Specifically, the production method (A) includes first preparing a raw material compound represented by the following general formula (10):

[Chem. 9]

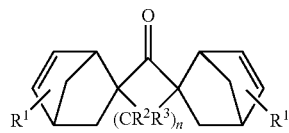

(10)

[in the formula (10), $R^1$, $R^2$, $R^3$, and n have the same definitions as those of $R^1$, $R^2$, $R^3$, and n in the general formula (1), respectively], followed by esterification to form a first ester compound represented by the following general formula (11):

[Chem. 10]

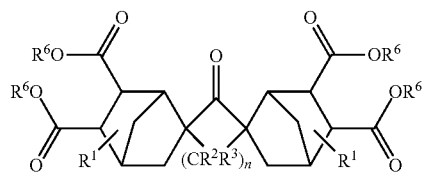

(11)

[$R^6$ each independently represent one selected from the group consisting of alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms, and n represents an integer of 0 to 12] (first ester compound formation step). Note that the first ester compound obtained as described above can contain six stereoisomers represented by the following general formulae (i) to (vi):

[Chem. 11]

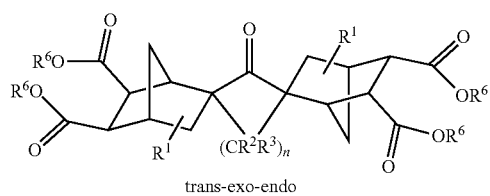

trans-exo-endo (i)

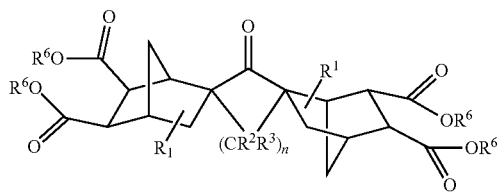

cis-exo-endo (ii)

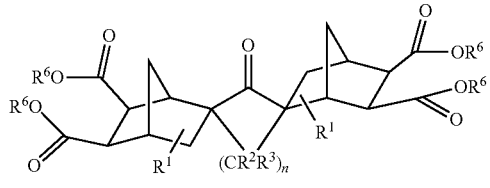

trans-exo-exo (iii)

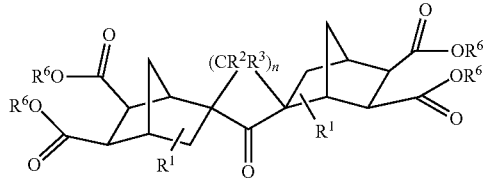

trans-endo-endo (iv)

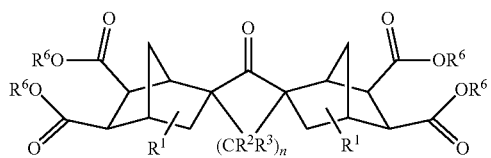

cis-exo-exo (v)

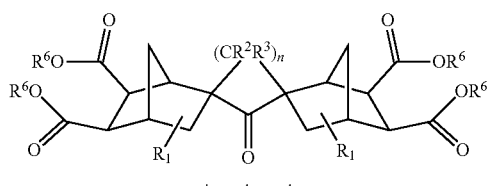

cis-endo-endo (vi)

[trans-exo-endo isomer: the formula (i); cis-exo-endo isomer: the formula (ii); trans-exo-exo isomer: the formula (iii); trans-endo-endo isomer: the formula (iv); cis-exo-exo isomer: the formula (v); and cis-endo-endo isomer: the formula (vi)]. Next, the method includes using the difference in solubility into a solvent between the stereoisomers contained in the formed first ester compound to extract isomers from the first ester compound such that the ratio of the summed amount of the trans-exo-endo isomer and the cis-exo-endo isomer is 50% by mole or more and that the content of the trans-exo-endo isomer is 30% by mole, to thereby obtain a second ester compound in which the ratio of the summed amount of the cis-exo-endo isomer is 50% by mole or more and the content of the trans-exo-endo isomer is 30% by mole or more (second ester compound production step). Subsequently, the method includes converting the second ester compound to an acid dianhydride to obtain the tetracarboxylic dianhydride of the present invention (tetracarboxylic dianhydride production step). Hereinafter, the production method (A) is described.

As described above, the production method (A) includes, in the first ester compound formation step, first preparing a raw material compound, followed by esterification to form a first ester compound.

The raw material compound is the compound represented by the general formula (10), and $R^1$, $R^2$, $R^3$, and n in the formula have the same definitions as those of $R^1$, $R^2$, $R^3$, and n in the general formula (1), respectively (preferred ones thereof are also the same). As the raw material compound, it is possible to preferably use ones same as those described in, for example, Japanese Unexamined Patent Application Publication No. 2015-137235, International Publication No. WO2011/099517, and the like. In addition, the method for producing the raw material compound is not particularly limited, and it is possible to appropriately use known methods (for example, methods described in JP 2015-137235 A, WO 2011/099517 A, and the like).

In addition, the method for esterifying the raw material compound is not particularly limited either, and it is possible to appropriately employ a method capable of introducing an ester group into a carbon atom forming a double bond of the raw material compound (method capable of alkoxycarbonylation). For example, it is possible to appropriately use a method described in International Publication No. WO2014/050810, a method described in Japanese Unexamined Patent Application Publication No. 2015-137231, a method described in Japanese Unexamined Patent Application Publication No. 2014-218460, a method described in WO 2011/099517 A, and the like. As described above, a known method can appropriately be employed as the esterification method. For example, it is possible to employ a method including reacting the raw material compound with an alcohol and carbon monoxide, followed by esterification to introduce an ester group into a carbon atom forming a double bond of the raw material compound.

The alcohol which can be used in esterification is not particularly limited, but is preferably an alcohol represented by the following general formula (12):

$$R^6OH \qquad (12)$$

[in the formula (12), $R^6$ has the same definition as that of $R^6$ in the general formula (11)]. Specifically, the alcohol used is preferably an alkyl alcohol having 1 to 10 carbon atoms (more preferably 1 to 5 and further preferably 1 to 3) (note that the alkyl group may be linear or branched), a cycloalkyl alcohol having 3 to 10 carbon atoms (more preferably 3 to 8 and further preferably 5 or 6), an alkenyl alcohol having 2 to 10 carbon atoms (more preferably 2 to 5 and further preferably 2 or 3), an aryl alcohol having 6 to 20 carbon atoms (more preferably 6 to 10 and further preferably 6 to 8), an aralkyl alcohol having 7 to 20 carbon atoms (more preferably 7 to 10 and further preferably 7 to 9). Of these alcohols, methanol and ethanol are more preferable, and methanol is particularly preferable, from the viewpoint that the obtained compound is easier to purify. In addition, one of these alcohols may be used alone, or two or more thereof may be used as a mixture.

By using such an alcohol to react the raw material compound with the alcohol ($R^6OH$) and carbon monoxide (CO), it is possible to introduce an ester group represented by the following general formula (13):

$$-COOR^6 \qquad (13)$$

[in the formula (13), $R^6$ has the same definition as that of $R^6$ in the general formula (11)] (the ester group may have the same or different $R^6$ for each introduction position) into a carbon atom forming a double bond in the raw material compound, thereby making it possible to form the first ester compound represented by the general formula (11). The conditions in the reaction (various conditions such as presence or absence of using a catalyst, an oxidizing agent, a solvent, and the like, the type thereof, and the reaction temperature) are not particularly limited, and it is possible to appropriately employ conditions employed in known esterification methods (for example, conditions described in WO 2014/050810 A, JP 2015-137231 A, JP 2014-218460 A, WO 2011/099517 A, and the like) (for example, the reaction may take place in the presence of a palladium catalyst and an oxidizing agent).

Moreover, from the viewpoint that the purification is easier, $R^6$ in the general formula (11) is each independently preferably a methyl group, an ethyl group, an n-propyl group, an isopropyl group, an n-butyl group, an isobutyl group, a sec-butyl, a t-butyl, a 2-ethylhexyl group, a cyclohexyl group, an allyl group, a phenyl group, or a benzyl group, and particularly preferably a methyl group. Note that $R^6$ in the general formula (11) may be the same or different, and is more preferably the same from the viewpoint of synthesis.

In addition, the production method (A) includes obtaining the first ester compound as a reaction product of the raw material compound, the alcohol ($R^6OH$), and carbon monoxide (CO) (note that the first ester compound can contain the six stereoisomers represented by the general formulae (i) to (vi)) and then, in the second ester compound production step, using the difference in solubility into a solvent between the stereoisomers contained in the first ester compound to extract isomers from the first ester compound such that the ratio of the summed amount of the trans-exo-endo isomer and the cis-exo-endo isomer is 50% by mole or more and that the content of the trans-exo-endo isomer is 30% by mole, to thereby obtain a second ester compound in which the ratio of the summed amount of the cis-exo-endo isomer is 50% by mole or more and the content of the trans-exo-endo isomer is 30% by mole or more.

Note that the present inventors have found that the six stereoisomers of the first ester compound have different solubilities to a solvent with the trans-exo-endo isomer and the cis-exo-endo isomer having relatively high solubilities to a solvent and that the following step using those characteristics makes it possible to obtain a second ester compound in which the ratio of the summed amount of the trans-exo-endo isomer and the cis-exo-endo isomer is 50% by mole or more and the content of the trans-exo-endo isomer is 30% by mole or more. Specifically, the raw material compound is reacted with the alcohol ($R^6OH$) and carbon monoxide (CO) to obtain the first ester compound as a reaction product. After that, the reaction product is first added into a solvent, and the reaction product is dissolved in the solvent under such a temperature condition that can dissolve the reaction product (optionally by stirring), to thereby obtain a dissolution liquid. Subsequently, the obtained dissolution liquid is cooled (may be allowed to naturally cool in the case of being heated) to precipitate crystals in the solution. After the precipitation of crystals, on the solution side, the trans-exo-endo isomer and the cis-exo-endo isomer having relatively high solubilities to a solvent remain at higher concentrations, and ester compounds with higher concentrations of the trans-exo-endo isomer and the cis-exo-endo isomer remain dissolved. On the other hand, on the crystal side, other isomers other than the trans-exo-endo isomer and the cis-exo-endo isomer (except for the trans-exo-exo isomer and the cis-exo-exo isomer originally contained only in small amounts) are likely to precipitate, and their crystals have relatively high concentrations of other isomers other than the trans-exo-endo isomer and the cis-exo-endo isomer. By filtering the resultant and collecting the filtrate side, not the crystal side, it is possible to extract a compound having a higher ratio of the summed amount of the trans-exo-endo isomer and the cis-exo-endo isomer (mixture of isomers). As described above, it is possible to extract isomers from the first ester compound such that the ratio of the summed amount of the trans-exo-endo isomer and the cis-exo-endo isomer is 50% by mole or more and that the content of the trans-exo-endo isomer is 30% by mole. As described above, by performing an operation involving dissolution of the reaction product in a solvent, cooling (naturally cooling in some cases) to precipitate crystals, and filtration to collect the filtrate (by performing the operation multiple times in some cases), it is possible to obtain a second ester compound in which the ratio of the summed amount of the cis-exo-endo isomer is 50% by mole or more and the content of the trans-exo-endo isomer is 30% by mole or more.

As described above, the solvent which can be used when extracting isomers from the first ester compound such that the ratio of the summed amount of the trans-exo-endo isomer and the cis-exo-endo isomer is 50% by mole or more and that the content of the trans-exo-endo isomer is 30% by mole is preferably one having high solubility to the trans-exo-endo isomer and the cis-exo-endo isomer, and examples thereof include aromatic solvents such as toluene, xylene, o-xylene, m-xylene, p-xylene, and benzene, hydrocarbon-based solvents such as pentane, hexane, heptane, cyclopentane, cyclohexane, and petroleum ether, alcohol-based solvents such as methanol, ethanol, isopropanol, butanol, diethylene glycol, and propylene glycol, ketone-based solvents such as acetone, methyl ethyl ketone, methyl isobutyl ketone, cyclopentanone, and cyclohexanone, ester-based solvents such as methyl acetate, ethyl acetate, isopropyl acetate, butyl acetate, and propylene glycol monoacetic acid ester, ether-based solvents such as diethyl ether, diisopropyl ether, tetrahydrofuran, dioxane, dioxolane, glyme, diglyme, and propylene glycol monomethyl ether, nitrile-based solvents such as acetonitrile and benzonitrile, polar solvents such as DMSO, DMF, DMAc, NMP, DMI, TMU, ethyl lactate, formic acid, acetic acid, and propionic acid, halogen-based solvents such as dichloromethane, chloroform, carbon tetrachloride, chlorobenzene, and dichlorobenzene, and mixture solvents thereof. In addition, of these solvents, toluene, xylene, benzene, ethanol, ethyl acetate, diisopropyl ether, acetonitrile, ethyl lactate, and acetic acid are preferable, toluene, ethanol, ethyl acetate, and acetic acid are more preferable, and toluene, ethyl acetate, and acetic acid are further preferable, from the viewpoint of isomer separation (extractability and crystallization separation).

In addition, the temperature condition employed when dissolving the reaction product in a solvent differs depending on the type of solvent and cannot be generally said, but is preferably 0 to 150° C. and more preferably 30 to 120° C. If the temperature condition is less than the lower limit, the first ester compound tends not to dissolve. Meanwhile, if the temperature condition exceeds the upper limit, deterioration or coloring tends to proceed. Note that, when dissolving the reaction product in a solvent, it is preferable to add the reaction product in a solvent followed by stirring from the viewpoint of more efficient dissolution.

In addition, when extracting isomers from the first ester compound, the crystals and the filtrate are separated by filtration, and the filtrate is collected. Note that the extraction step for isomers may include rinsing the crystals, separated by filtration, with the solvent for rinse washing, collecting the rinse washing liquid, mixing with the filtrate, and collecting the resultant. The rinse washing makes it possible to collect the solution adhering to and remaining on the crystals and to extract the trans-exo-endo isomer and the cis-exo-endo isomer with the rinse washing liquid even when they are precipitated on the crystal surfaces. Therefore, it is possible to efficiently collect the trans-exo-endo isomer and the cis-exo-endo isomer having higher solubilities to a solvent. Note that, by collecting the filtrate as described above and then vaporizing the solvent, it is possible to obtain the second ester compound as a solid content. Note that, in the case where the solid content obtained as described above is an ester compound which does not satisfy the conditions that the ratio of the summed amount of the trans-exo-endo isomer and the cis-exo-endo isomer is 50% by mole or more and that the content of the trans-exo-endo isomer is 30% by mole or more, the second ester compound may be allowed to have a desired isomer concentration by repeatedly performing the above operation (operation of dissolving in a solvent, precipitating crystals, and collecting the filtrate) so as to satisfy the above conditions.

In addition, the production method (A) includes obtaining the second ester compound and then, in the tetracarboxylic dianhydride production step, converting the second ester compound to an acid dianhydride to obtain the tetracarboxylic dianhydride of the present invention. Note that, since the acid dianhydride conversion step does not change the three-dimensional configuration of norbornane rings, it is possible to obtain a tetracarboxylic dianhydride which satisfies the conditions that the ratio of the summed amount of the trans-exo-endo isomer and the cis-exo-endo isomer is 50% by mole or more and that the content of the trans-exo-endo isomer is 30% by mole or more.

The method for converting the second ester compound to an acid dianhydride is not particularly limited, and it is possible to appropriately employ a known method capable of obtaining a tetracarboxylic dianhydride by converting a tetraester compound to an acid dianhydride. For example, it is possible to appropriately employ a method and the like including heating the second ester compound in a carboxylic acid having 1 to 5 carbon atoms. As a method for converting a tetraester compound to an acid dianhydride, it is possible to appropriately employ, for example, methods and conditions employed in a method described in International Publication No. WO2014/050788, a method described in International Publication No. WO2015/178261, a method described in WO 2011/099518 A, a method described in Japanese Unexamined Patent Application Publication No. 2015-218160, and the like (it is possible to appropriately use a method employed in the above known methods also in terms of various conditions including the used carboxylic acid, catalyst, and the like).

In addition, after converting the second ester compound to an acid dianhydride as described above to form a tetracarboxylic dianhydride satisfying the above conditions, the tetracarboxylic dianhydride may be washed by using the solvent (one explained as a solvent which can be used when extracting isomers from the first ester compound). Note that, depending on the conditions employed in the washing step, it is also possible to further vary the ratios of isomers in the tetracarboxylic dianhydride. For example, although it differs depending on the type of solvent, consider the case of washing using a solvent at about 15° C. or above as a washing liquid. The isomers easily dissolve in the washing liquid, and some of the isomers tend to be removed with washing, which causes the ratios of isomers in the tetracarboxylic dianhydride to vary. Note that, regarding the type of isomer which easily dissolves in the washing liquid, the cis-exo-endo isomer of an acid dianhydride tends to relatively easy dissolve, although it is impossible to generally say since it differs depending on the type of washing liquid (solvent), temperature condition, and the like. In addition, for example, although it differs depending on the type of solvent, consider the case of washing using a solvent at a lower temperature (for example, at about −5° C. or below) as the washing liquid. It is possible to carry out the washing step while more efficiently suppressing the dissolution of the isomers in the solvent (while more sufficiently maintaining the isomer ratios). As described above, by obtaining a tetracarboxylic dianhydride satisfying the above conditions followed by further washing by appropriately changing the type of solvent, temperature condition, and the like depending on the intended design, it is possible to redesign to a tetracarboxylic dianhydride having the desired isomer ratios.

As described above, by converting the second ester compound to an acid dianhydride, it is possible to obtain the tetracarboxylic dianhydride represented by the general formula (1) wherein the ratio of the summed amount of the stereoisomer (A) and the stereoisomer (B) is 50% by mole or more relative to the total amount of the stereoisomers (summed amount of all stereoisomers contained in the tetracarboxylic dianhydride), and the content ratio of the stereoisomer (A) is 30% by mole or more relative to the total amount of the stereoisomers (summed amount of all stereoisomers contained in the tetracarboxylic dianhydride).

Hereinabove, the tetracarboxylic dianhydride of the present invention has been described. Next, a polyimide precursor resin of the present invention is described.

[Polyimide Precursor Resin]

A polyimide precursor resin of the present invention is a polyimide precursor resin in which a ratio of a summed amount of a repeating unit (A') represented by the general formula (4) and a repeating unit (B') represented by the general formula (5) is 50% by mole or more relative to a total amount of all repeating units, and a content ratio of the repeating unit (A') is 30% by mole or more relative to the total amount of all the repeating units.

In the general formulae (4) and (5), $R^1$, $R^2$, and $R^3$ each independently represent one selected from the group consisting of a hydrogen atom, alkyl groups having 1 to 10 carbon atoms, and a fluorine atom, n represents an integer of 0 to 12, $R^4$ represents an arylene group having 6 to 50 carbon atoms, and X each independently represent one selected from the group consisting of a hydrogen atom, alkyl groups having 1 to 6 carbon atoms, and alkyl silyl groups having 3 to 9 carbon atoms.

$R^1$, $R^2$, $R^3$, and n in the general formulae (4) and (5) have the same definitions as those of $R^1$, $R^2$, $R^3$, and n in the general formula (1), respectively (preferred ones thereof are also the same).

The arylene group which can be selected as $R^4$ in the general formulae (4) and (5) is one having 6 to 50 carbon atoms, and the number of the carbon atoms of the aryl group is preferably 6 to 40, more preferably 6 to 30, and further preferably 12 to 20. If the number of carbon atoms is less than the lower limit, the heat resistance of the obtained polyimide tends to decrease. Meanwhile, if the number of carbon atoms exceeds the upper limit, the solubility of the obtained polyimide to a solvent tends to decrease.

From the viewpoint of the balance between heat resistance and solubility, $R^4$ in the general formulae (4) and (5) is preferably at least one of groups represented by the following general formulae (a) to (d):

[Chem. 12]

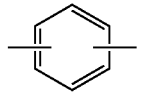
(a)

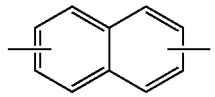
(b)

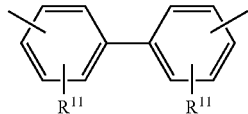
(c)

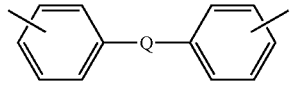
(d)

[in the formula (c), $R^1$ represents one selected from the group consisting of a hydrogen atom, a fluorine atom, a methyl group, an ethyl group, a hydroxyl group, and a trifluoromethyl group, and in the formula (d), Q represents one selected from the group consisting of a 9,9-fluorenylidene group; groups represented by formulae: —O—, —S—, —CO—, —CONH—, —SO$_2$—, —C(CF$_3$)$_2$—, —C(CH$_3$)$_2$—, —CH$_2$—, —O—C$_6$H$_4$—C(CH$_3$)$_2$—C$_6$H$_4$—O—, —O—C$_6$H$_4$—C(CF$_3$)$_2$—C$_6$H$_4$—O—, —O—C$_6$H$_4$—SO$_2$—C$_6$H$_4$—O—, —C(CH$_3$)$_2$—C$_6$H$_4$—C(CH$_3$)$_2$—O—C$_6$H$_4$—C$_6$H$_4$—O—, —CONH—C$_6$H$_4$—NHCO—, —NHCO—C$_6$H$_4$—CONH—, —C$_6$H$_4$—, and —O—C$_6$H$_4$—O—; and a group represented by the following general formula (e):

[Chem. 13]

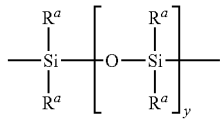
(e)

(in the formula (e), $R^a$ each independently represent one of an alkyl group having 1 to 10 carbon atoms, a phenyl group, and a tolyl group, and y represents an integer of 1 to 18)].

$R^1$ in the general formula (c) is more preferably a hydrogen atom, a fluorine atom, a methyl group, or an ethyl group, and particularly preferably a hydrogen atom from the viewpoint of heat resistance. Moreover, $R^{11}$ in the general formula (c) is more preferably a methyl group, a hydroxyl group, or a trifluoromethyl group from the viewpoint of solubility. In addition, in the group represented by the general formula (e) which can be selected as Q in the general formula (d), $R^a$ is each independently one of an alkyl group having 1 to 10 carbon atoms, a phenyl group, and a tolyl group. If the number of carbon atoms of the alkyl group exceeds the upper limit, the heat resistance and transparency of the polyimide film tend to decrease. $R^a$ is preferably a methyl group, an ethyl group, a propyl group, an isopropyl group, a phenyl group, and a tolyl group, more preferably a methyl group and an ethyl group, and further preferably a methyl group. In addition, y in the general formula (e)

represents an integer of 1 to 15 (more preferably 3 to 12 and further preferably 5 to 10). If the value of y is less than the lower limit, the adhesion and laser removability of the polyimide film (easiness of removing a film when laser removing processing is performed in the case of producing the film on a substrate) tend to decrease. Meanwhile, if the value of y exceeds the upper limit, the heat resistance and transparency of the polyimide film tend to decrease.

In addition, from the viewpoint of the balance between heat resistance and solubility, Q in the general formula (d) is preferably a 9,9-fluorenylidene group; or a group represented by a formula: —CONH—, —O—$C_6H_4$—O—, —O—, —C($CH_3$)$_2$—, —O—$C_6H_4$—$SO_2$—$C_6H_4$—O—, —$CH_2$—, —O—$C_6H_4$—$C_6H_4$—O—, or —O—$C_6H_4$—C($CH_3$)$_2$—$C_6H_4$—O—, particularly preferably a group represented by a formula: —CONH—, —O—$C_6H_4$—O—, —O—$C_6H_4$—$C_6H_4$—O—, or —O—, and most preferably a group represented by a formula: —CONH—, —O—$C_6H_4$—O—, or —O—. Moreover, Q in the general formula (d) is preferably the group represented by the general formula (e) from the viewpoint of adhesion and laser removability, and is preferably the group represented by the formula: —CONH— from the viewpoint of linear expansion coefficient and heat resistance.

In addition, from the viewpoint of higher solubility to a solvent, $R^4$ is preferably a divalent group (arylene group) formed by removing two amino groups from an aromatic diamine selected from the group consisting of 9,9-bis(4-aminophenyl)fluorene, 4,4'-diaminodiphenylmethane, 4,4'-diaminodiphenyl ether, 2,2-bis(4-aminophenoxyphenyl)propane, bis[4-(3-aminophenoxy)phenyl]sulfone, bis[4-(4-aminophenoxy)phenyl]sulfone, 2,2'-bis(trifluoromethyl)-4,4'-diaminobiphenyl, 2,2'-dimethyl-4,4'-diaminobiphenyl, 1,3-bis(4-aminophenoxy)benzene, 1,3-bis(3-aminophenoxy)benzene, and 2,2-bis(4-aminophenoxyphenyl)propane, more preferably a divalent group (arylene group) formed by removing two amino groups from an aromatic diamine selected from the group consisting of bis[4-(3-aminophenoxy)phenyl]sulfone, 1,3-bis(3-aminophenoxy)benzene, 2,2-bis(4-aminophenoxyphenyl)propane, 2,2'-bis(trifluoromethyl)-4,4'-diaminobiphenyl, 2,2'-dimethyl-4,4'-diaminobiphenyl, 1,3-bis(4-aminophenoxy)benzene, and 4,4'-diaminodiphenyl ether, and further preferably a divalent group (arylene group) formed by removing two amino groups from an aromatic diamine selected from the group consisting of 2,2-bis(4-aminophenoxyphenyl)propane, 2,2'-bis(trifluoromethyl)-4,4'-diaminobiphenyl, and bis[4-(3-aminophenoxy)phenyl]sulfone.

X in the general formulae (4) and (5) each independently represent one selected from the group consisting of a hydrogen atom, alkyl groups having 1 to 6 carbon atoms (preferably 1 to 3 carbon atoms), and alkyl silyl groups having 3 to 9 carbon atoms.

Regarding X, the type of the substituent and the introduction rate of the substituent can be changed by appropriately changing the production conditions thereof. When both of X are hydrogen atoms (in the case of a repeating unit of polyamic acid), the production of a polyimide tends to be easy. In addition, when X is an alkyl group having 1 to 6 carbon atoms (preferably 1 to 3 carbon atoms), the storage stability of the polyimide precursor resin tends to be better. In addition, when X is an alkyl group having 1 to 6 carbon atoms (preferably 1 to 3 carbon atoms), X is more preferably a methyl group or an ethyl group. In addition, when X is an alkyl silyl group having 3 to 9 carbon atoms, the solubility of the polyimide precursor resin tends to be better. In addition, when X is an alkyl silyl group having 3 to 9 carbon atoms, X is more preferably a trimethylsilyl group or a t-butyldimethylsilyl group.

When X in the formulae is a group other than a hydrogen atom (an alkyl group and/or an alkyl silyl group), the introduction rate of the group is not particularly limited. However, when at least some of X are alkyl groups and/or alkyl silyl groups (when some of X in the repeating unit (A') and/or the repeating unit (B') contained in the resin precursor are alkyl groups and/or alkyl silyl groups), the alkyl groups and/or the alkyl silyl groups are preferably 25% or more (more preferably 50% or more and further preferably 75% or more) relative to the total amount (total number) of X (note that, in this case, X other than the alkyl groups and/or the alkyl silyl groups are hydrogen atoms). When the alkyl groups and/or the alkyl silyl groups are 25% or more relative to the total amount (total number) of X of the repeating unit contained in the resin precursor, the storage stability of the polyimide precursor resin tends to be better. The polyimide precursor resin is preferably such that both of X are hydrogen atoms, that is, a polyamic acid from the viewpoint of easier production of a polyimide.

In addition, in the polyimide precursor resin of the present invention, the ratio of the summed amount of the repeating unit (A') and the repeating unit (B') needs to be 50% by mole or more relative to the total amount of all repeating units. If the ratio of the summed amount of the repeating units (A') and (B') is less than the lower limit, the solubility of the polyimide obtained from the polyimide precursor resin to a solvent decreases. In addition, the ratio of the summed amount of the repeating units (A') and (B') is more preferably 50 to 100% by mole, further preferably 60 to 98% by mole, particularly preferably 70 to 95% by mole, and most preferably 80 to 90% by mole. If the ratio of the summed amount of the repeating units (A') and (B') is in the above range, the solubility of the finally obtained polyimide to a solvent tends to be good.

In the polyimide precursor resin of the present invention, the content ratio of the repeating unit (A') represented by the general formula (4) needs to be 30% by mole or more relative to the total amount of all repeating units. If the content ratio of the repeating unit (A') is less than the lower limit, the solubility of the polyimide obtained from the polyimide precursor resin to a solvent decreases. In addition, the content ratio of the repeating unit (A') is more preferably 30 to 99% by mole, further preferably 40 to 90% by mole, particularly preferably 50 to 85% by mole, and most preferably 60 to 80% by mole relative to the total amount of all repeating units. If the content ratio of the repeating unit (A') is in the above range, the polyimide tends to have higher solubility while having sufficiently high levels of heat resistance and transparency.

In the polyimide precursor resin of the present invention, the content ratio of the repeating unit (B') represented by the general formula (5) is more preferably 1 to 70% by mole, further preferably 10 to 60% by mole, particularly preferably 10 to 50% by mole, and most preferably 10 to 40% by mole relative to the total amount of all repeating units. If the content ratio of the repeating unit (B') is in the above range, the polyimide tends to have higher solubility while having sufficiently high levels of heat resistance and transparency.

Note that the repeating unit (A') is derived from the stereoisomer (A) of the tetracarboxylic dianhydride represented by the general formula (1) (compound represented by the general formula (2): trans-exo-endo isomer) and from the aromatic diamine represented by the formula: $H_2N$—$R^4$—$NH_2$ ($R^4$ in the formula has the same definition as that of $R^4$ in the general formulae (4) and (5)). As described above, the three-dimensional structure of the repeating unit (A') is a structure derived from the three-dimensional structure of the stereoisomer (A) of the tetracarboxylic dianhydride, and the repeating unit (A') is a repeating unit having a trans-exo-endo three-dimensional structure. In addition, the repeating unit (B') is derived from the stereoisomer (B) of the tetracarboxylic dianhydride represented by the general formula (1) (compound represented by the general formula (3): cis-exo-endo isomer) and from the aromatic diamine represented by the formula: $H_2N-R^4-NH_2$ ($R^4$ in the formula has the same definition as that of $R^4$ in the general formulae (4) and (5)), and is a repeating unit having a cis-exo-endo three-dimensional structure. Moreover, a repeating unit of the polyimide precursor resin derived from a stereoisomer of the tetracarboxylic dianhydride represented by the general formula (1) other than the stereoisomers (A) and (B) and from the formula: $H_2N-R^4-NH_2$ is as follows. Specifically, the repeating unit derived from the above-mentioned trans-exo-exo isomer (compound represented by the formula (I)) is a repeating unit (C') having a trans-exo-exo three-dimensional structure represented by the following general formula (I'), the repeating unit derived from the above-mentioned trans-endo-endo isomer (compound represented by the formula (II)) is a repeating unit (D') having a trans-endo-endo three-dimensional structure represented by the following general formula (II'), the repeating unit derived from the above-mentioned cis-exo-exo isomer (compound represented by the formula (III)) is a repeating unit (E') having a cis-exo-exo three-dimensional structure represented by the following general formula (III'), and the repeating unit derived from the cis-endo-endo isomer (compound represented by the formula (IV)) is a repeating unit (F') having a cis-endo-endo three-dimensional structure represented by the following general formula (IV'). Note that $R^1$, $R^2$, $R^3$, $R^4$, and n in the following general formulae (I') to (IV') have the same definitions as those of $R^1$, $R^2$, $R^3$, $R^4$, and n in the general formulae (4) and (5), respectively (preferred ones thereof are also the same)

[Chem. 14]

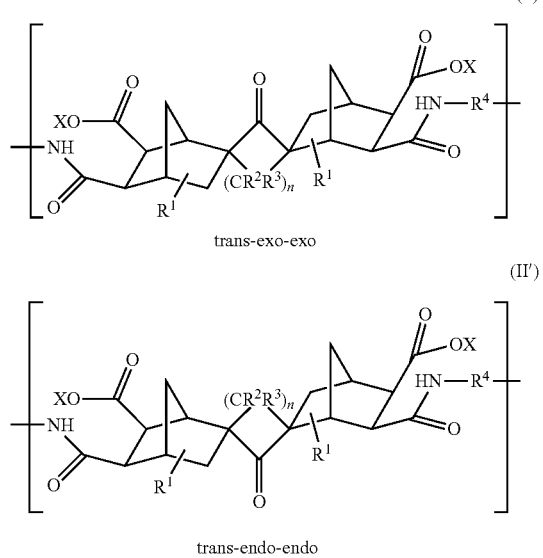

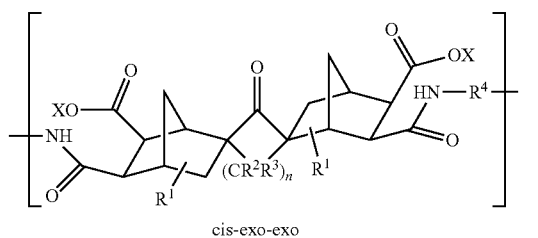

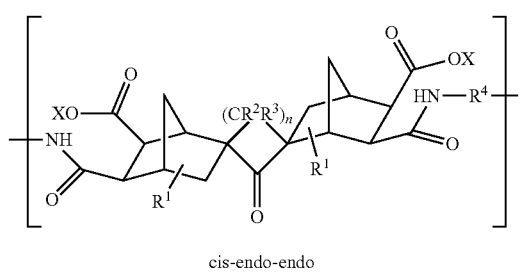

In addition, the polyimide precursor resin of the present invention may contain additional repeating units other than the repeating units (A') and (B') as long as the effects of the present invention are not impaired, and the additional repeating units are preferably the repeating units (C') to (F') because they can be easily prepared using the tetracarboxylic dianhydride of the present invention.

In the case of containing the repeating unit (D') and/or (F'), the ratio (ratio based on mole) of the summed amount of the repeating units (D') and (F') is preferably 50% by mole or less, more preferably 0 to 40% by mole, further preferably 0 to 30% by mole, and particularly preferably 0 to 20% by mole relative to all repeating units. If the ratio of the summed amount of the repeating units (D') and (F') exceeds the upper limit, the solubility of the finally obtained polyimide in a solvent tends to decrease.

Moreover, in the case of containing the repeating unit (C') and/or (E'), the ratio (ratio based on mole) of the summed amount of the repeating units (C') and (E') is preferably 10% by mole or less, more preferably 0 to 5% by mole, further preferably 0 to 3% by mole, particularly preferably 0 to 1.5% by mole, and most preferably 0 to 1% by mole relative to all repeating units. If the ratio of the summed amount of the repeating units (C') and (E') exceeds the upper limit, the physical properties of the finally obtained polyimide tend to deteriorate.

In addition, the polyimide precursor resin (more preferably a polyamic acid) may contain, as the additional repeating unit described above, an additional repeating unit other than the repeating units (A') to (F'). In the polyimide precursor resin, from the viewpoint of more sufficiently exhibiting the effects of the present invention, the total amount of the repeating units (A') to (F') is preferably 70 to 100% by mole, more preferably 80 to 100% by mole, further preferably 90 to 100% by mole, particularly preferably 95 to 100% by mole, and most preferably and 98 to 100% by mole relative to all repeating units. Note that, from the viewpoint of higher solubility to a solvent, the polyimide precursor resin preferably contains 100% by mole of the repeating units (A') to (F').

In addition, the additional repeating unit other than the repeating units (A') to (F') is not particularly limited, and examples thereof include known repeating units which can be used as a polyimide precursor resin (more preferably a repeating unit of a polyamic acid). As the additional repeating unit other than the repeating units (A') to (F'), one may use, for example, a repeating unit derived from an additional tetracarboxylic dianhydride other than the tetracarboxylic dianhydride represented by the general formula (1) (for example, the compounds described in paragraph [0171] of WO 2014/034760 A, and the like), or the like.

In addition, the polyimide precursor resin of the present invention is, from the viewpoint of easier preparation, preferably a reaction product (polymer) of the tetracarboxylic dianhydride of the present invention and an aromatic diamine represented by the formula: $H_2N$—$R^4$—$NH_2$ ($R^4$ in the formula has the same definition as that of $R^4$ in the general formulae (4) and (5)).

In addition, the polyamic acid preferable as the polyimide precursor resin has an intrinsic viscosity [η] of preferably 0.05 to 3.0 dL/g and more preferably 0.1 to 2.0 dL/g. If the intrinsic viscosity [η] is less than 0.05 dL/g, a film obtained when a film-shaped polyimide is produced by using the polyamic acid tends to be brittle. Meanwhile, if the intrinsic viscosity [η] exceeds 3.0 dL/g, the processability deteriorates because of the excessively high viscosity, and when, for example, a film is produced, it is difficult to obtain a uniform film. In addition, the intrinsic viscosity [η] can be measured as follows. Specifically, first, by using N,N-dimethylacetamide as a solvent, a measurement sample (solution) is obtained by dissolving the polyamic acid in the N,N-dimethylacetamide to a concentration of 0.5 g/dL. Next, by using the measurement sample, the viscosity of the measurement sample is measured with a kinematic viscometer under a temperature condition of 30° C., and the thus determined value is employed as the intrinsic viscosity [η]. Note that an automatic viscometer manufactured by RIGO CO., LTD. (trade name: "VMC-252") is used as the kinematic viscometer.

In addition, the polyimide precursor resin (more preferably a polyamic acid) can be preferably used in the production of the polyimide of the present invention. In addition, the polyimide precursor resin (more preferably a polyamic acid) can be obtained as a reaction intermediate (precursor) in the production of the polyimide of the present invention.

Hereinabove, the polyimide precursor resin of the present invention (more preferably a polyamic acid) has been described. Next, a polyimide of the present invention is described.

[Polyimide]

A polyimide of the present invention is a polyimide in which a ratio of a summed amount of a repeating unit (A) represented by the general formula (6) and a repeating unit (B) represented by the general formula (7) is 50% by mole or more relative to a total amount of all repeating units, and a content ratio of the repeating unit (A) is 30% by mole or more relative to the total amount of all the repeating units.

In the general formulae (6) and (7), $R^1$, $R^2$, and $R^3$ each independently represent one selected from the group consisting of a hydrogen atom, alkyl groups having 1 to 10 carbon atoms, and a fluorine atom, n represents an integer of 0 to 12, and $R^4$ represents an arylene group having 6 to 50 carbon atoms. $R^1$, $R^2$, $R^3$, and n in the general formulae (6) and (7) have the same definitions as those of $R^1$, $R^2$, $R^3$, and n in the general formula (1), respectively (preferred ones thereof are also the same). In addition, $R^4$ in the general formulae (6) and (7) has the same definition as that of $R^4$ in the general formulae (4) and (5) (preferred ones thereof are also the same).

In addition, in the polyimide of the present invention, the ratio of the summed amount of the repeating unit (A) and the repeating unit (B) needs to be 50% by mole or more relative to the total amount of all repeating units. If the ratio of the summed amount of the repeating units (A) and (B) is less than the lower limit, the solubility of the polyimide to a solvent decreases. In addition, the ratio of the summed amount of the repeating units (A) and (B) is more preferably 50 to 100% by mole, further preferably 60 to 98% by mole, particularly preferably 70 to 95% by mole, and most preferably 80 to 90% by mole. If the ratio of the summed amount of the repeating units (A) and (B) is in the above range, the solubility of the polyimide to a solvent tends to be good.

In the polyimide of the present invention, the content ratio of the repeating unit (A) represented by the general formula (2) needs to be 30% by mole or more relative to the total amount of all repeating units. If the content ratio of the repeating unit (A) is less than the lower limit, the solubility of the polyimide to a solvent decreases. In addition, the content ratio of the repeating unit (A) is more preferably 30 to 99% by mole, further preferably 40 to 90% by mole, particularly preferably 50 to 85% by mole, and most preferably 60 to 80% by mole. If the content ratio of the repeating unit (A) is in the above range, the polyimide tends to have higher solubility while having sufficiently high levels of heat resistance and transparency.

In the polyimide of the present invention, the content ratio of the repeating unit (B) represented by the general formula (7) is more preferably 1 to 70% by mole, further preferably 10 to 60% by mole, particularly preferably 10 to 50% by mole, and most preferably 10 to 40% by mole relative to the total amount of all repeating units. If the content ratio of the repeating unit (B) is in the above range, the polyimide tends to have higher solubility while having sufficiently high levels of heat resistance and transparency.

Note that the repeating unit (A) is derived from the stereoisomer (A) of the tetracarboxylic dianhydride represented by the general formula (1) (compound represented by the general formula (2): trans-exo-endo isomer) and from the aromatic diamine represented by the formula: $H_2N$—$R^4$—$NH_2$ ($R^4$ in the formula has the same definition as that of $R^4$ in the general formulae (4) and (5)). As described above, the three-dimensional structure of the repeating unit (A) is a structure derived from the three-dimensional structure of the stereoisomer (A) of the tetracarboxylic dianhydride, and the repeating unit (A) is a repeating unit having a trans-exo-endo three-dimensional structure. In addition, the repeating unit (B) is derived from the stereoisomer (B) of the tetracarboxylic dianhydride represented by the general formula (1) (compound represented by the general formula (3): cis-exo-endo isomer) and from the aromatic diamine represented by the formula: $H_2N$—$R^4$—$NH_2$ ($R^4$ in the formula has the same definition as that of $R^4$ in the general formulae (4) and (5)), and is a repeating unit having a cis-exo-endo three-dimensional structure. Moreover, a repeating unit of the polyimide derived from a stereoisomer of the tetracarboxylic dianhydride represented by the general formula (1) other than the stereoisomers (A) and (B) and from the formula: $H_2N$—$R^4$—$NH_2$ is as follows. Specifically, the repeating unit derived from the above-mentioned trans-exo-exo isomer (compound represented by the formula (I)) is a repeating unit (C) having a trans-exo-exo three-dimensional structure represented by the following general formula (I-1), the repeating unit derived from the above-mentioned trans-endo-endo isomer (compound represented by the formula (II-1)) is a repeating unit (D) having a trans-endo-endo three-dimensional structure represented by the following general formula (II), the repeating unit derived from the above-mentioned cis-exo-exo isomer (compound represented by the formula (III)) is a repeating unit (E) having a cis-exo-exo three-dimensional structure represented by the following general formula (III-1), and the repeating unit derived from the cis-endo-endo isomer (compound represented by the formula (IV)) is a repeating unit (F) having a cis-endo-endo three-dimensional structure represented by the following general formula (IV-1). Note that $R^1$, $R^2$, $R^3$, $R^4$, and n in the following general formulae (I-1) to (IV-1) have the same definitions as those of $R^1$, $R^2$, $R^3$, $R^4$, and n in the general formulae (6) and (7), respectively (preferred ones thereof are also the same).

[Chem. 15]

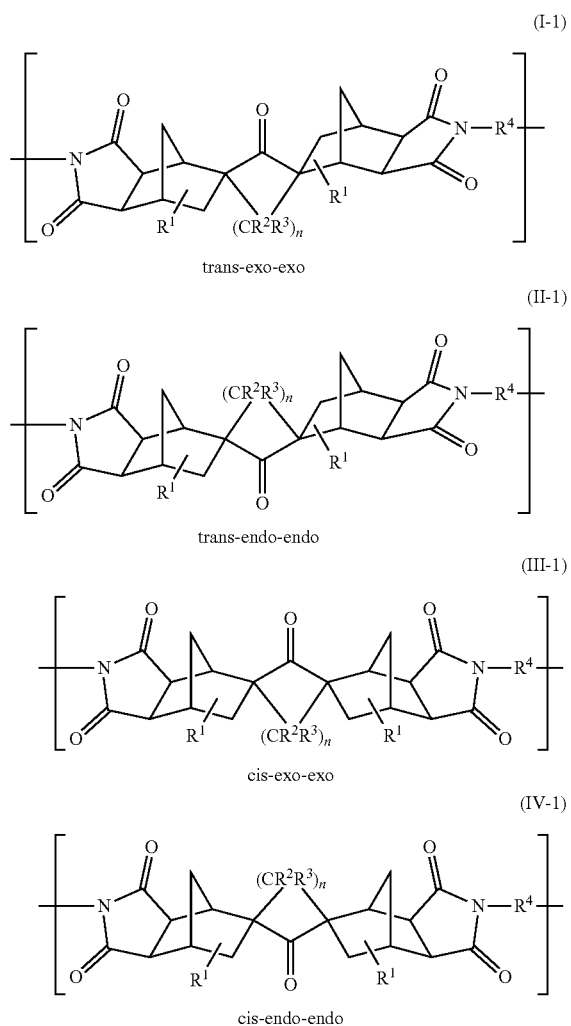

In addition, the polyimide of the present invention may contain additional repeating units other than the repeating units (A) and (B) as long as the effects of the present invention are not impaired. In addition, since the polyimide of the present invention can be efficiently prepared by using the tetracarboxylic dianhydride of the present invention, the additional repeating units other than the repeating units (A) and (B) are preferably the repeating units (C) to (F).

In the case of containing the repeating unit (D) and/or (F), the ratio (ratio based on mole) of the summed amount of the repeating units (D) and (F) is preferably 50% by mole or less, more preferably 0 to 40% by mole, further preferably 0 to 30% by mole, and particularly preferably 0 to 20% by mole relative to all repeating units. If the ratio of the summed amount of the repeating units (D) and (F) exceeds the upper limit, the solubility of the polyimide in a solvent tends to decrease.

Moreover, in the case of containing the repeating unit (C) and/or (E), the ratio (ratio based on mole) of the summed amount of the repeating units (C) and (E) is preferably 10% by mole or less, more preferably 0 to 5% by mole, further preferably 0 to 3% by mole, particularly preferably 0 to 1.5% by mole, and most preferably 0 to 1% by mole relative to all repeating units. If the ratio of the summed amount of the repeating units (C) and (E) exceeds the upper limit, the physical properties of the polyimide tend to deteriorate.

In addition, the polyimide may contain, as the additional repeating unit described above, an additional repeating unit other than the repeating units (A) to (F). The additional repeating unit other than the repeating units (A) to (F) is not particularly limited, and examples thereof include known repeating units which can be used as a polyimide repeating unit. As the additional repeating unit other than the repeating units (A) to (F), one may use, for example, a repeating unit derived from an additional tetracarboxylic dianhydride other than the tetracarboxylic dianhydride represented by the general formula (1) (for example, the compounds described in paragraph [0171] of WO 2014/034760 A, and the like), or the like.

In addition, the polyimide of the present invention is, from the viewpoint of easier preparation, preferably a reaction product (polymer) of the tetracarboxylic dianhydride of the present invention and an aromatic diamine represented by the formula: $H_2N—R^4—NH_2$ ($R^4$ in the formula has the same definition as that of $R^4$ in the general formulae (4) and (5)).

In addition, the polyimide of the present invention is preferably one having a 5% weight loss temperature of 400° C. or above, and more preferably 450 to 550° C. If the 5% weight loss temperature is less than the lower limit, there is a tendency that a sufficient heat resistance is difficult to achieve. Meanwhile, if the 5% weight loss temperature exceeds the upper limit, it tends to be difficult to produce a polyimide having such a characteristic. The 5% weight loss temperature can be determined by, for example, heating the scan temperature from 30° C. to 550° C. at a rate of temperature rise of 10° C./min under the condition of a nitrogen gas atmosphere and measuring the temperature at which the weight loss of the sample used reaches 5% by use of a TG/DTA7200 thermogravimetric analyzer (manufactured by SII NanoTechnology Inc.).

In addition, the polyimide is one having a glass transition temperature (Tg) of preferably 250° C. or above and more preferably 300 to 500° C. If the glass transition temperature (Tg) is less than the lower limit, there is a tendency that a sufficient heat resistance is difficult to achieve. Meanwhile, if the glass transition temperature (Tg) exceeds the upper limit, it tends to be difficult to produce a polyimide having such a characteristic. Note that the glass transition temperature (Tg) can be measured by using a thermomechanical analyzer (manufactured by Rigaku Corporation under the trade name of "TMA8310" or "TMA8311") in a tensile mode. Specifically, the glass transition temperature (Tg) can be determined by using a thermomechanical analyzer (manufactured by Rigaku Corporation under the trade name of "TMA8310" or "TMA8311") as a measuring apparatus, forming a polyimide film of 20 mm in length and 5 mm in width (the thickness of the film is not particularly limited because it does not affect the measured value, but is preferably 5 to 80 µm) as a measurement sample, employing the conditions of a tensile mode (49 mN) and a rate of temperature rise of 5° C./min under a nitrogen atmosphere followed by measurement and determination of a TMA curve, and extrapolating the curves before and after the inflection point of the TMA curve due to glass transition.

Moreover, the polyimide is one having a softening temperature of preferably 300° C. or above and more preferably 350 to 550° C. If the softening temperature is less than the lower limit, there is a tendency that a sufficient heat resistance is difficult to achieve. Meanwhile, if the softening temperature exceeds the upper limit, it tends to be difficult to produce a polyimide having such a characteristic. Note that the softening temperature can be measured by using a thermomechanical analyzer (manufactured by Rigaku Corporation under the trade name of "TMA8310" or "TMA8311") in a penetration mode. In addition, in the measurement, since the size of the sample (length, width, thickness, and the like) does not affect the measured value, the size of the sample may be appropriately adjusted to a size which can be mounted on a jig of the thermomechanical analyzer (manufactured by Rigaku Corporation under the trade name of "TMA8310" or "TMA8311") to be used.

In addition, the polyimide is one having a thermal decomposition temperature (Td) of preferably 450° C. or above and more preferably 480 to 600° C. If the thermal decomposition temperature (Td) is less than the lower limit, there is a tendency that a sufficient heat resistance is difficult to achieve. Meanwhile, if the thermal decomposition temperature (Td) exceeds the upper limit, it tends to be difficult to produce a polyimide having such a characteristic. Note that the thermal decomposition temperature (Td) can be determined by using a TG/DTA7200 thermogravimetric analyzer (manufactured by SII NanoTechnology Inc.) to measure the temperature at the intersection of a tangent drawn on the decomposition curve before and after the thermal decomposition under a nitrogen atmosphere and under the condition of a rate of temperature rise of 10° C./min.

In addition, the polyimide of the present invention has, in pencil hardness, a hardness of preferably 6B to 6H and a hardness of more preferably HB to 4H. If the hardness is less than the lower limit, it tends to be difficult to obtain a sufficiently high level of hardness. Meanwhile, if the hardness exceeds the upper limit, it tends to be difficult to produce a colorless and transparent polyimide having such a characteristic. Note that the value of the pencil hardness can be determined by measurement in accordance with the method specified in JIS K5600-5-4 issued in 1999.

Moreover, the number average molecular weight (Mn) of the polyimide is preferably 1000 to 1000000 and more preferably 10000 to 500000 in terms of polystyrene. If the number average molecular weight is less than the lower limit, there is a tendency that the film obtained in the case of forming a film using the polyimide is brittle and that the heat resistance of the obtained polyimide decreases. Meanwhile, if the number average molecular weight exceeds the upper limit, there is a tendency that the viscosity increases and it takes a long period of time to dissolve the polyimide in a solvent, resulting in processing difficulty and that a flexible film cannot be obtained in the case of forming a film using the polyimide, resulting in wrinkles in the film.

In addition, the weight average molecular weight (Mw) of the polyimide is preferably 1000 to 5000000 in terms of polystyrene. The lower limit value of the numeric range of the weight average molecular weight (Mw) is more preferably 5000, further preferably 10000, and particularly preferably 20000. In addition, the upper limit value of the numeric range of the weight average molecular weight (Mw) is more preferably 5000000, further preferably 500000, and particularly preferably 100000. If the weight average molecular weight is less than the lower limit, there is a tendency that the film obtained in the case of forming a film using the polyimide is brittle and that the heat resistance of the obtained polyimide decreases. Meanwhile, if the weight average molecular weight exceeds the upper limit, there is a tendency that it takes a long period of time to dissolve the polyimide in a solvent, resulting in processing difficulty and that a flexible film cannot be obtained in the case of forming a film using the polyimide, resulting in wrinkles in the film.

Moreover, the molecular weight distribution (Mw/Mn) of the polyimide is preferably 1.1 to 5.0 and more preferably 1.5 to 3.0. If the molecular weight distribution is less than the lower limit, production tends to be difficult. Meanwhile, if the molecular weight distribution exceeds the upper limit, it tends to be difficult to obtain a uniform film. Note that the molecular weight (Mw or Mn) and the molecular weight distribution (Mw/Mn) of the polyimide can be determined by converting the data measured using, as a measuring apparatus, a gel permeation chromatography (GPC) measuring apparatus (degasser: DG-2080-54 manufactured by JASCO Corporation, feed pump: PU-2080 manufactured by JASCO Corporation, interface: LC-NetII/ADC manufactured by JASCO Corporation, column: GPC column KF-806M (×2) manufactured by Shodex, column oven: 860-CO manufactured by JASCO Corporation, RI detector: RI-2031 manufactured by JASCO Corporation, column temperature 40° C., chloroform solvent (flow rate 1 mL/min)) in terms of polystyrene.

In addition, the polyimide has an intrinsic viscosity [η] of preferably 0.05 to 3.0 dL/g and more preferably 0.1 to 2.0 dL/g. If the intrinsic viscosity [η] is less than 0.05 dL/g, a film obtained when a film-shaped polyimide is produced by using the polyimide tends to be brittle. Meanwhile, if the intrinsic viscosity [η] exceeds 3.0 dL/g, the processability deteriorates because of the excessively high viscosity, and when, for example, a film is produced, it is difficult to obtain a uniform film. In addition, the intrinsic viscosity [η] can be measured as follows. Specifically, first, by using N,N-dimethylacetamide as a solvent, a measurement sample (solution) is obtained by dissolving the polyimide in the N,N-dimethylacetamide to a concentration of 0.5 g/dL. Next, by using the measurement sample, the viscosity of the measurement sample is measured with a kinematic viscometer under a temperature condition of 30° C., and the thus determined value is employed as the intrinsic viscosity [η]. Note that an automatic viscometer manufactured by RIGO CO., LTD. (trade name: "VMC-252") is used as the kinematic viscometer.

In addition, the polyimide has a linear expansion coefficient (CTE) of preferably 0 to 100 ppm/K and more preferably 10 to 70 ppm/K. If the linear expansion coefficient exceeds the upper limit, peeling tends to easily occur due to the thermal history in the case of forming a composite in combination with a metal or an inorganic material having a linear expansion coefficient in a range of 5 to 20 ppm/K. Meanwhile, if the linear expansion coefficient is less than the lower limit, there is a tendency that the solubility decreases and the film characteristic deteriorates.

As a method for measuring the linear expansion coefficient of the polyimide, the method described below is employed. Specifically, first, a polyimide film having a size of 20 mm in length and 5 mm in width (the thickness of the film is not particularly limited because it does not affect the measured value, but is preferably 5 to 80 μm) is formed as a measurement sample. Then, a thermomechanical analyzer (manufactured by Rigaku Corporation under the trade name of "TMA8310" or "TMA8311") is used as a measuring apparatus. The conditions of a tensile mode (49 mN) and a rate of temperature rise of 5° C./min under a nitrogen atmosphere are employed. The temperature is raised from room temperature to 200° C. (first temperature rise), and after allowed to cool to 30° C. or below, the temperature is raised from that temperature to 400° C. (second temperature rise). The change in the longitudinal length of the sample at the time of the temperature rise is measured. Subsequently, the TMA curve obtained by the measurement at the time of the second temperature rise (measurement during the temperature rise from the cooled temperature to 400° C.) is used to determine the average value of the changes in length per 1° C. in the temperature range of 100° C. to 200° C., and the obtained value is measured as the linear expansion coefficient of the polyimide. As described above, the linear expansion coefficient of the polyimide of the present invention employed is a value obtained by determining the average value of the changes in length per 1° C. in the temperature range of 100° C. to 200° C. based on the TMA curve.

In addition, when a film is formed from the polyimide, the film is preferably one having a sufficiently high transparency, and more preferably one having a total luminous transmittance of 80% or more (further preferably 82% or more, and particularly preferably 83% or more). Such a total luminous transmittance can be easily achieved by selecting, as appropriate, the type of the polyimide repeating unit and the like. In addition, the polyimide is one having a haze (turbidity) of more preferably 5 to 0 (further preferably 4 to 0 and particularly preferably 3 to 0) from the viewpoint of obtaining higher colorlessness and transparency. If the value of the haze exceeds the upper limit, it tends to be difficult to achieve higher levels of colorlessness and transparency. Moreover, the polyimide is one having a yellowness index (YI) of more preferably 10 to 0 (further preferably 5 to 0 and particularly preferably 3 to 0) from the viewpoint of obtaining higher colorlessness and transparency. If the yellowness index exceeds the upper limit, it tends to be difficult to achieve higher levels of colorlessness and transparency. As the total luminous transmittance, the haze (turbidity), and the yellowness index (YI), it is possible to employ values measured using, as a sample for measurement, a film made of polyimide having a thickness of about 13 μm (range of 13 μm±2 μm: basically no variation in the range. Note that the thickness of the measurement sample is more preferably 13 μm) by use of a measuring apparatus manufactured by NIPPON DENSHOKU INDUSTRIES CO., LTD. under the trade name of "Haze Meter NDH-5000" or manufactured by NIPPON DENSHOKU INDUSTRIES CO., LTD. under the trade name of "Spectrometer SD6000" (Note that the total luminous transmittance and the haze are measured using the trade name "Haze Meter NDH-5000" manufactured by NIPPON DENSHOKU INDUSTRIES CO., LTD., and the yellowness index is measured using the trade name "Spectrometer SD6000" manufactured by NIPPON DENSHOKU INDUSTRIES CO., LTD.). In addition, the sizes in length and width of the measurement sample may be such sizes that can be disposed at a measurement position of the measuring apparatus. The sizes in length and width may be changed as appropriate. Note that the total luminous transmittance is determined by performing measurement in accordance with JIS K7361-1 (issued in 1997), the haze (turbidity) is determined by performing measurement in accordance with JIS K7136 (issued in 2000), and the yellowness index (YI) is determined by performing measurement in accordance with ASTM E313-05 (issued in 2005).

In the polyimide, the absolute value of retardation (Rth) in the thickness direction measured at a wavelength of 590 nm is, in terms of a thickness of 10 μm, preferably 200 nm or less, more preferably 150 nm or less, further preferably 100 nm or less, and particularly preferably 50 nm or less. Specifically, the value of retardation (Rth) is preferably −200 nm to 200 nm (more preferably −150 nm to 150 nm, further preferably −100 to 100 nm, and particularly preferably −50 to 50 nm). If the absolute value of retardation (Rth) in the thickness direction exceeds the upper limit, there is a tendency that the contrast decreases and the viewing angle decreases when used in a display device. Note that, if the absolute value of retardation (Rth) is in the above range, the effect of suppressing the decrease in contrast and the effect of improving the viewing angle tend to be higher when used in a display device. As described, the absolute value of retardation (Rth) in the thickness direction is preferably a lower value from the viewpoint that it is possible to suppress the decrease in contrast to a higher extent and to further improve the viewing angle when used in a display device.

The "absolute value of retardation (Rth) in the thickness direction" can be determined by using a measuring apparatus manufactured by AXOMETRICS, Inc. under the trade name of "AxoScan," inputting the value of the refractive index (589 nm) of the polyimide film measured as described later into the measuring apparatus, then using light having a wavelength of 590 nm under the conditions of temperature: 25° C. and humidity: 40% to measure the retardation in the thickness direction of the polyimide film, determining a value (converted value) converted to a retardation value per 10 μm of film thickness based on the measured value determined of retardation in the thickness direction (measured value by automatic measurement (automatic calculation) of the measuring apparatus), and calculating the absolute value from the converted value. As described above, the "absolute value of retardation (Rth) in the thickness direction" can be determined by calculating the absolute value of the converted value (|converted value|). Note that the size of the polyimide film as measurement sample is not particularly limited as long as it is larger than the photometric unit of the stage of the measuring instrument (diameter: about 1 cm), but preferably has a size of length: 76 mm, width 52 mm, and thickness 5 to 20 μm.

In addition, the value of the "refractive index (589 nm) of the polyimide film" used in the measurement of retardation (Rth) in the thickness direction is determined by forming an unstretched film made of the same type of polyimide as the polyimide forming the film to be measured for retardation, then using the unstretched film as a measurement sample (note that, when the film to be measured is an unstretched film, the film can be used as a measurement sample as it is), and using a refractive index-measuring apparatus as a measuring apparatus (manufactured by Atago Co., Ltd. under the trade name of "NAR-1T SOLID") to measure the average refractive index of the measurement sample for light of 589 nm at a temperature condition of 23° C. by use of a light source of 589 nm. As described above, an unstretched film is used to measure the value of the "refractive index (589 nm) of the polyimide film," and the obtained measured value (value of the average refractive index of the measurement sample for the light of 589 nm) is used for the measurement of the above-described retardation (Rth) in the thickness direction. Here, the size of the polyimide film as the measurement sample is not particularly limited as long as it can be used for the refractive index-measuring apparatus, and may be a size of 5 to 20 μm in thickness in 1 cm square (1 cm in length and width).

The shape of the polyimide is not particularly limited, and may be, for example, the shape of a film, the form of powder, moreover the shape of a pellet by extrusion molding, and the like. As described above, the polyimide of the present invention can be formed into various shapes as appropriate by a known method such as in the shape of a film and in the shape of a pellet by extrusion molding.

In addition, such a polyimide is especially useful as a material for producing films for flexible wiring boards, heat-resistant insulating tapes, enameled wires, protective coating agents for semiconductors, liquid crystal orientation films, transparent electrically conductive films for organic ELs, flexible substrate films, flexible transparent electrically conductive films, transparent electrically conductive films for organic thin film-type solar cells, transparent electrically conductive films for dye-sensitized-type solar cells, flexible gas barrier films, films for touch panels, TFT substrate films for flat panel detectors, seamless polyimide belts (so-called transfer belts) for copiers, transparent electrode substrates (transparent electrode substrates for organic ELs, transparent electrode substrates for solar cells, transparent electrode substrates for electronic paper, and the like), interlayer insulating films, sensor substrates, substrates for image sensors, reflectors for light-emitting diodes (LED) (reflectors for LED illumination: LED reflectors), covers for LED illumination, covers for LED reflector illumination, coverlay films, highly extensible composite substrates, resists for semiconductors, lithium-ion batteries, substrates for organic memories, substrates for organic transistors, substrates for organic semiconductors, color filter base materials, and the like. In addition, the polyimide can be used as appropriate in, for example, parts for automobiles, aerospace parts, bearing parts, sealing materials, bearing parts, gearwheels, valve parts, and the like in addition to the aforementioned applications by e.g. forming the shape into the form of powder and into various formed bodies.

Hereinabove, the polyimide of the present invention has been described. Next, description is provided for a method which can be preferably used as a method for producing a polyimide and a polyimide precursor resin of the present invention.

<Method of Producing Polyimide of Present Invention>

The method for producing a polyimide of the present invention is not particularly limited, and it is possible to preferably employ a method including reacting the tetracarboxylic dianhydride of the present invention with an aromatic diamine represented by the formula: $H_2N-R^4-NH_2$ [$R^4$ in the formula is an arylene group having 6 to 50 carbon atoms, and has the same definition as that of $R^4$ in the general formulae (4) and (5) (preferred ones thereof are also the same)] in the presence of a polymerization solvent, to thereby obtain the polyimide of the present invention (hereinafter simply referred to as the "Polyimide Production Method (I)" for convenience). As described, the polyimide of the present invention can be obtained as a reaction product of the tetracarboxylic dianhydride of the present invention and the aromatic diamine. In the Polyimide Production Method (I), a specific step of obtaining a polyimide by reacting the tetracarboxylic dianhydride of the present invention and the aromatic diamine is not particularly limited.

In addition, the Polyimide Production Method (I) may be, for example, a method including a step (Ia) of reacting the tetracarboxylic dianhydride of the present invention with an aromatic diamine represented by the formula: $H_2N-R^4-NH_2$ in the presence of a polymerization solvent, to thereby obtain the polyimide precursor resin of the present invention in which both of X in each of the general formulae (4) and (5) are hydrogen atoms (polyamic acid which is preferable as the polyimide precursor resin of the present invention), and a step (Ib) of imidizing the polyimide precursor resin (polyamic acid), to thereby obtain the polyimide of the present invention. Hereinafter, description is provided for the steps (Ia) and (Ib) which can be preferably used in the method for producing a polyimide of the present invention.

(Step (Ia): Step of Obtaining Polyamic Acid)

The step (Ia) is a step of reacting the tetracarboxylic dianhydride of the present invention with an aromatic diamine represented by the formula: $H_2N-R^4-NH_2$ in the presence of a polymerization solvent, to thereby obtain the polyamic acid (polyimide precursor resin of the present invention in which both of X in each of the general formulae (4) and (5) are hydrogen atoms).

The step of obtaining a polyamic acid uses, as monomer components, the tetracarboxylic dianhydride of the present invention and the aromatic diamine represented by the formula: $H_2N-R^4-NH_2$. Since the tetracarboxylic dianhydride of the present invention is the tetracarboxylic dianhydride represented by the general formula (1) satisfying the conditions that the ratio of the summed amount of the stereoisomers (A) and (B) is 50% by mole or more relative to the total amount of the stereoisomers (summed amount of all stereoisomers contained in the tetracarboxylic dianhydride) and that the content ratio of the stereoisomer (A) is 30% by mole or more relative to the total amount of the stereoisomers (summed amount of all stereoisomers contained in the tetracarboxylic dianhydride), it is possible to, based on the three-dimensional structure thereof, prepare the polyamic acid which is preferable as the polyimide precursor resin of the present invention (polyimide precursor resin of the present invention in which both of X in each of the general formulae (4) and (5) are hydrogen atoms).

In addition, regarding the aromatic diamine represented by the formula: $H_2N-R^4-NH_2$, $R^4$ is an arylene group having 6 to 50 carbon atoms, and has the same definition as that of $R^4$ in the general formulae (4) and (5) (preferred ones thereof are also the same). As the aromatic diamine, it is possible to appropriately use, for example, the aromatic diamines described in paragraph [0211] of International Publication No. WO2017/030019, the aromatic diamines described in paragraph [0157] of WO 2014/034760 A, and the like. In addition, as the aromatic diamines, a commercially available one can be used as appropriate. One of those aromatic diamines may be used alone or two or more thereof may be used in combination depending on the design of the intended polyimide.

In addition, the polymerization solvent is preferably an organic solvent capable of dissolving both the tetracarboxylic dianhydride and the aromatic diamine. As the organic solvent, it is possible to appropriately use a known polymerization solvent which can be used in the production of a polyimide or a polyamic acid (organic solvent: for example, organic solvents described in paragraph [0213] of International Publication No. WO2017-030019, and the like). From the viewpoint of solubility in the tetracarboxylic dianhydride and the aromatic diamine, the polymerization solvent used is more preferably an aprotic polar solvent, more preferably a solvent containing N,N-dimethylacetamide (which may be composed only of N,N-dimethylacetamide or may be combined with other solvents), and among others particularly preferably a combination of N,N-dimethylacetamide and γ-butyrolactone. As described above, in the case of using the combination of N,N-dimethylacetamide and γ-butyrolactone as the polymerization solvent, it is possible to allow the polymerization reaction to more efficiently proceed (achieve a state which allows the reaction to more easily proceed), thereby making it possible to obtain a polyamic acid varnish having a high degree of polymerization in a shorter period of time. One of those organic solvents may be used alone or two or more thereof may be used in combination.

In addition, the step (Ia) may further include adding a basic compound to the organic solvent in the reaction of the tetracarboxylic dianhydride with the aromatic diamine from the viewpoint of improving the reaction rate and obtaining a polyamic acid having a high degree of polymerization. The basic compound is not particularly limited, and is, for empurple, triethylamine, tetrabutylamine, tetrahexylamine, 1,8-diazabicyclo[5.4.0]-undecene-7, pyridine, isoquinoline, α-picoline, and the like. In addition, the amount of the basic compound used is preferably 0.001 to 10 equivalents and more preferably 0.01 to 0.1 equivalents relative to 1 equivalent of the tetracarboxylic dianhydrides.

In addition, in the step (Ia), it is possible to appropriately employ the conditions employed in a known method for producing a polyamic acid as the ratio of the tetracarboxylic dianhydride and the aromatic diamine used, the amount of the polymerization solvent (organic solvent) used, the reaction temperature and the reaction time for reacting the tetracarboxylic dianhydride and the aromatic diamine, and the like. For example, the ratio of the tetracarboxylic dianhydride and the aromatic diamine used is such that the amount of all acid anhydride groups in the tetracarboxylic dianhydride used in the reaction is preferably 0.2 to 2 equivalents (more preferably 0.3 to 1.2 equivalents) relative to 1 equivalent of the amino groups in the aromatic diamine. In addition, the amount of the polymerization solvent (organic solvent) used in the step (Ia) is such an amount that the total amount of the tetracarboxylic dianhydride and the aromatic diamine is preferably 0.1 to 50% by mass (more preferably 10 to 30% by mass) relative to the total amount of the reaction solution. In addition, the reaction temperature in the reaction may be appropriately adjusted to a temperature which enables reaction of these compounds and is not particularly limited, but is, depending on the case, preferably −40 to 450° C., more preferably −20 to 400° C., further preferably −20 to 200° C., and particularly preferably 0 to 100° C.

As described above, the method for reacting the tetracarboxylic dianhydride and the aromatic diamine employed may be, for example, a method including dissolving the aromatic diamine in a solvent under an inert atmosphere of nitrogen, helium, argon, or the like under atmospheric pressure, then adding the tetracarboxylic dianhydride at the above-described reaction temperature, and then allowing the reaction to proceed for 10 to 48 hours; a method including adding the aromatic diamine and the tetracarboxylic dianhydride to a reaction vessel under an inert atmosphere of nitrogen, helium, argon, or the like under atmospheric pressure, then adding a solvent to dissolve the components in the solvent, and then allowing the reaction to proceed for 10 to 48 hours at the above-described reaction temperature; and the like.

As described above, by carrying out the step (Ia), it is possible to obtain a polyamic acid in which both of X in each of the general formulae of the repeating units (A') and (B') are hydrogen atoms, the ratio of the summed amount of the repeating units (A') and (B') is 50% by mole or more relative to the total amount of all repeating units, and the content ratio of the repeating unit (A') is 30% by mole or more relative to the total amount of all repeating units. Note that the polyamic acid thus obtained is the same as the polyamic acid described as a preferable one in the polyimide precursor resin of the present invention.

Note that, in the case of allowing the finally obtained polyimide to contain an additional repeating unit together with the repeating units (A) and (B), the polyimide may be produced by, in the step (Ia), using an additional tetracarboxylic dianhydride together with the tetracarboxylic dianhydride of the present invention to react these with the aromatic diamine, using an additional diamine together with the aromatic diamine to react these with the tetracarboxylic dianhydride of the present invention, or further appropriately using both the additional tetracarboxylic dianhydride and the additional diamine, for example. As the additional tetracarboxylic dianhydride and the additional aromatic diamine, it is possible to appropriately use known ones used in the production of a polyimide.

(Step (Ib): Step of Obtaining Polyimide)

The step (Ib) is a step of imidizing the polyamic acid, to thereby obtain the polyimide of the present invention.

The method for imidizing a polyamic acid may be a method capable of imidizing a polyamic acid and is not particularly limited, and it is possible to appropriately employ a known method. For example, as the method for imidizing a polyamic acid, it is possible to employ a method (Ib-1) for imidizing the polyamic acid using a so-called imidization agent, a method (Ib-2) for imidizing the polyamic acid by heat treatment, and the like.

The above-described method (Ib-1) of imidization using an imidization agent is not particularly limited, and it is possible to appropriately use a known method capable of imidizing a polyamic acid using an imidization agent (including various conditions such as the temperature condition, the pressure condition, the atmosphere condition, the type of imidization agent, the amount of imidization agent used, and the reaction time) For example, it is possible to appropriately employ methods described in International Publication No. WO2015-163314, WO 2014/034760 A, and the like. In addition, in the method (Ib-1), it is also possible to appropriately use an additive and the like used in known methods in combination with an imidization agent (for example, a reaction accelerator (such as an acid scavenger), an azeotropic dehydration agent, and the like), and their use method, types, and the like may be the same as those of known conditions (for example, conditions described in WO 2015-163314 A, WO 2014/034760 A, and the like) (for example, a catalytic amount of reaction accelerator (such as DMAP) and azeotropic dehydration agent (such as benzene, toluene, or xylene) may be added to azeotropically remove the water generated when the polyamic acid becomes an imide, followed by chemical imidization). Note that, from the viewpoints of reactivity, availability, and practicability, the imidization agent is preferably acetic anhydride, propionic anhydride, and trifluoroacetic anhydride, more preferably acetic anhydride and propionic anhydride, and further preferably acetic anhydride. In addition, in the case of using a reaction accelerator in combination, the reaction accelerator is preferably triethylamine, diisopropylethylamine, N-methylpiperidine, and pyridine, more preferably triethylamine, pyridine, and N-methylpiperidine, and further preferably triethylamine and N-methylpiperidine from the viewpoints of reactivity, availability, and practicability.

In addition, the method (Ib-2) of imidization by heat treatment is not particularly limited, and it is possible to appropriately use a known method capable of imidizing a polyamic acid by heat treatment (including various conditions such as the temperature condition, the atmosphere condition, the type of imidization agent, and the amount of imidization agent used). For example, it is possible to appropriately employ methods described in WO 2015-163314 A, WO 2014/034760 A, and the like. In addition, the method (Ib-2) of imidization by heat treatment is a method of imidization by performing heat treatment on the polyamic acid at a temperature condition of preferably 60 to 450° C. (more preferably 80 to 400° C.) from the viewpoint of allowing the reaction to efficiently proceed. In addition, the reaction time (heating time) in the case of employing the method of imidization by the heat treatment is preferably set to 0.5 to 5 hours.

In addition, in the case of imidization by the heat treatment, a so-called reaction accelerator may be used to accelerate high molecular weight formation and imidization. As the reaction accelerator, a known reaction accelerator (such as tertiary amine) may be appropriately used. In addition, from the viewpoints of reactivity, availability, and practicability, the reaction accelerator is preferably triethylamine, diisopropylethylamine, N-methylpiperidine, and pyridine, more preferably triethylamine, pyridine, and N-methylpiperidine, and further preferably triethylamine and N-methylpiperidine. One of those reaction accelerators may be used alone or two or more thereof may be used in combination. In addition, the amount of the reaction accelerator used is preferably 0.01 to 4.0 moles, more preferably 0.05 to 2.0 moles, and further preferably 0.05 to 1.0 moles relative to 1 mole of the repeating units in the polyamic acid.

In addition, when the method (Ib-2) in which the imidization is conducted by a heat treatment is employed for the imidization in a case where the method comprising these step (Ia) and the step (Ib) is used, the following method may be employed. Specifically, after the step (Ia) is conducted, the reaction liquid obtained by reacting the tetracarboxylic dianhydride with the aromatic diamine in the organic solvent (the reaction liquid comprising the polyamic acid) is directly used without isolation of the polyamic acid. The solvent is removed from the reaction liquid by subjecting the reaction liquid to a treatment (solvent removal treatment) for removing the solvent by evaporation, and then the imidization is conducted by the heat treatment. This treatment for removing the solvent by evaporation makes it possible to, when a mold is used, create a form based on the mold, or to, when applied on a base material, create a form in the shape of a film or the like for isolation, followed by heat treatment to obtain a polyimide in the desired form, and the like. As described above, when a polyimide in the form of a film is produced, the obtained reaction liquid may be directly applied onto a base material (for example, a glass plate), followed by the treatment for removing the solvent by evaporation and the heat treatment. Thus, a polyimide in the form of a film can be produced by a simple method.

The temperature condition in the method of treatment (solvent removal treatment) of removing the solvent by evaporation is preferably 0 to 180° C. and more preferably 30 to 150° C. from the viewpoint of efficiently removing the solvent while sufficiently suppressing the generation of air bubbles and voids. Note that a method for applying the reaction liquid is not particularly limited, and a known method (such as a cast method) can be employed, as appropriate. In addition, when the polyamic acid is used after isolation from the reaction liquid, a method for the isolation is not particularly limited, and a known method capable of isolating a polyamic acid can be employed, as appropriate. For example, a method may be employed in which the polyamic acid is isolated as a reprecipitation product.

In addition, in the case of employing the method (Ib-2) of imidization by heat treatment, the step (Ia) and the step (Ib) may be simultaneously carried out as continuous steps. As described above, as the method for simultaneously carrying out the step (Ia) and the step (Ib) as continuous steps, it is possible to employ, for example, a method including performing heat treatment at the stage of reacting the tetracarboxylic dianhydride with the aromatic diamine and allowing the formation of polyamic acid (intermediate) and the subsequent formation of polyimide (imidization) to simultaneously proceed, to thereby simultaneously carrying out the step (Ia) and the step (Ib).

In addition, in the case of performing heat treatment when reacting the tetracarboxylic dianhydride with the aromatic diamine to simultaneously carry out the step (Ia) and the step (Ib) as described above, it is preferable to form a polyimide by using a reaction accelerator at the stage of reacting the tetracarboxylic dianhydride with the aromatic diamine in the presence of a polymerization solvent, and by heating and reacting the tetracarboxylic dianhydride and the aromatic diamine in the presence of the polymerization solvent and the reaction accelerator. In the case of simultaneously carrying out the step (Ia) and the step (Ib) as described above, heating continuously causes the generation of polyamic acid in the step (Ia) and the imidization of polyamic acid in the step (Ib), and a polyimide is prepared in the solvent. Here, by using the reaction accelerator, the reaction rates of the generation and imidization of polyamic acid become very fast, making it possible to more efficiently increase (extend) the molecular weight. In addition, in the case of heating by use of the reaction accelerator to simultaneously carry out the step (Ia) and the step (Ib), it is also possible to allow the reaction to efficiently proceed without using a so-called condensation agent (dehydration condensation agent) because heating makes it possible to cause the reaction between the tetracarboxylic dianhydride and the aromatic diamine to proceed and also to remove by evaporation the water generated by the reaction.

In addition, in the case of forming a polyimide by heating and reacting the tetracarboxylic dianhydride with the aromatic diamine in the presence of the polymerization solvent and the reaction accelerator (in the case of heating by use of the reaction accelerator to simultaneously carry out the step (Ia) and the step (Ib)), the temperature condition during the heating is preferably 100 to 250° C., more preferably 120 to 250° C., and further preferably 150 to 220° C. If the temperature condition is less than the lower limit, the reaction temperature is equal to or below the boiling point of water and thus no removal by distillation of water takes place, and the presence of water inhibits the progress of the reaction, which tends to make it difficult to more increase the molecular weight of the polyimide. Meanwhile, if the temperature condition exceeds the upper limit, a side reaction such as thermal decomposition of the solvent takes place, which increases impurities in the mixture liquid (varnish) of the polyimide and the organic solvent obtained after heating. Thus, when this mixture liquid is used to form a film, the physical properties of the obtained polyimide tend to deteriorate.

In addition, in the case of heating by use of the reaction accelerator to simultaneously carry out the step (Ia) and the step (Ib), the reaction accelerator used in the steps is preferably a tertiary amine such as triethylamine, diisopropylethylamine, N-methylpiperidine, pyridine, collidine, lutidine, 2-hydroxypyridine, 4-dimethylaminopyridine (DMAP), 1,4-diazabicyclo[2.2.2]octane (DABCO), diazabicyclononene (DBN), or diazabicycloundecene (DBU) Among these, triethylamine, diisopropylethylamine, N-methylpiperidine, and pyridine are preferable, triethylamine, pyridine, and N-methylpiperidine are more preferable, and triethylamine and N-methylpiperidine are further preferable from the viewpoints of reactivity, availability, and practicability. One of those reaction accelerators may be used alone or two or more thereof may be used in combination. As described above, in the case of heating by use of the reaction accelerator to simultaneously carry out the step (Ia) and the step (Ib), the amount of the reaction accelerator used is preferably 0.01 to 10 parts by mass and more preferably 0.05 to 2 parts by mass relative to 100 parts by mass of the total amount (summed amount) of the tetracarboxylic dianhydride and the aromatic diamine.

Note that, in the case of heating by use of the reaction accelerator to simultaneously carry out the step (Ia) and the step (Ib) followed by formation of a polyimide, it is also possible to obtain a polyimide in the shape of a film by, for example, applying a reaction liquid obtained after heating (reaction liquid containing the above-described polyimide) on various substrates to form a coating film, followed by removal of the solvent from the coating film and subsequent heat-curing. The heating condition in the heat-curing step is a condition of heating at a temperature condition of preferably 50 to 450° C. (more preferably 50 to 300° C.) for 1 to 5 hours. If the heating condition (temperature and time condition) is less than the lower limit, the solvent cannot be sufficiently dried, and the heat resistance of the film tends to decrease. Meanwhile, if the heating condition exceeds the upper limit, there is a tendency that a side reaction such as oxidation of terminal amino groups may proceed to lower the transparency.

As described above, it is possible to obtain the polyimide of the present invention in which the ratio of the summed amount of the repeating units (A) and (B) is 50% by mole or more relative to the total amount of all repeating units, and the content ratio of the repeating unit (A) is 30% by mole or more relative to the total amount of all repeating units.

<Method of Producing Polyimide Precursor Resin>

The polyimide precursor resin of the present invention can be classified into 1) a polyamic acid (both of X in each of the general formulae are hydrogen atoms), 2) a polyamic acid ester (at least some of X in the general formulae of the repeating units are alkyl groups), and 3) a polyamic acid silyl ester (at least some of X in the general formulae of the repeating units are alkyl silyl groups) according to the type of substituent X in the formulae of the repeating units. Thus, methods which can be preferably employed as a method for producing the polyimide precursor resin of the present invention are described separately for the classifications 1) to 3) of the polyimide precursor resin. Note that the method for producing the polyimide precursor resin of the present invention is not limited to the following production methods.

1) Polyamic Acid

Hereinafter, a method which can be preferably used to produce the polyamic acid is briefly described. A method which can be preferably used to produce the polyamic acid is not particularly limited, but is preferably a method including the step (Ia) described in the method for producing the polyimide of the present invention. Specifically, the method which can be preferably used to produce the polyamic acid is preferably a method including reacting the tetracarboxylic dianhydride with the aromatic diamine in the presence of a polymerization solvent, to thereby obtain the polyamic acid. Note that the conditions and the like for such reaction are as described above.

2) Polyamic Acid Ester

A method which can be preferably used to produce the polyamic acid ester is described below. Specifically, the method includes first reacting the tetracarboxylic dianhydride with any alcohol to obtain a diester dicarboxylic acid, followed by reaction with a chlorinating reagent (such as thionyl chloride or oxalyl chloride) to obtain a diester dicarboxylic acid chloride (derivative of a tetracarboxylic acid). When a monomer component containing the diester dicarboxylic acid chloride thus obtained (component containing the diester dicarboxylic acid chloride derived from the tetracarboxylic dianhydride of the present invention and optionally the tetracarboxylic dianhydride of the present invention) and the aromatic diamine are reacted by stirring in the range of −20 to 120° C. (more preferably −5 to 80° C.) for 1 to 72 hours, a polyimide precursor resin is obtained in which at least some of X in the formulae of the repeating units are alkyl groups. Note that, in the case of reaction at a stirring temperature of 80° C. or above, the molecular weight is likely to vary depending on the temperature history during polymerization, and imidization may be caused by heat. Thus, it tends to be difficult to stably produce the polyimide precursor resin. In addition, the polyimide precursor resin composed of the polyamic acid ester is easily obtained also by dehydration condensation of the diester dicarboxylic acid and the aromatic diamine using a phosphorus-based condensation agent, a carbodiimide condensation agent, or the like. Since the polyimide precursor resin composed of the polyamic acid ester obtained by such a method is stable, purification such as reprecipitation is also possible by adding a solvent such as water or alcohol.

3) Polyamic Acid Silyl Ester

Hereinafter, methods which can be preferably used to produce the polyamic acid silyl ester are briefly described by dividing into a so-called indirect method and direct method.

<Indirect Method>

As a method which can be preferably used to produce a polyamic acid silyl ester, it is possible to employ the method as below (indirect method). Specifically, first, the aromatic diamine and a silylating agent are reacted to obtain a silylated product of the aromatic diamine. Note that one may purify the silylated aromatic diamine by distillation or the like as needed. Next, a solution is obtained by dissolving the silylated aromatic diamine or a mixture of the silylated aromatic diamine and the aromatic diamine (not silylated) in a dehydrated solvent. Subsequently, the tetracarboxylic dianhydride is gradually added to the solution while stirring the solution. When the solution is stirred in the range of 0 to 120° C. (preferably 5 to 80° C.) for 1 to 72 hours, it is possible to obtain a polyimide precursor resin composed of the polyamic acid silyl ester in which at least some of X in the formulae of the repeating units are alkyl silyl groups. Note that, in the case of reaction at a stirring temperature of 80° C. or above, the molecular weight is likely to vary depending on the temperature history during polymerization, and imidization may be caused by heat. Thus, it tends to be difficult to stably produce the polyimide precursor resin.

Note that, as the silylating agent, it is preferable to use a silylating agent which does not contain chlorine atoms. Use of a silylating agent which does not contain chlorine atoms as described above eliminates the necessity of purifying the silylated aromatic diamine, making it possible to further simplify the steps. The silylating agent which does not contain chlorine atoms includes N,O-bis(trimethylsilyl)trifluoroacetamide, N,O-bis(trimethylsilyl)acetamide, and hexamethyldisilazane. In addition, the silylating agent is particularly preferably N,O-bis(trimethylsilyl)acetamide and hexamethyldisilazane because they do not contain fluorine atoms and are inexpensive.

In addition, in the silylation reaction of an aromatic diamine, it is possible to use an amine-based catalyst such as pyridine, piperidine, or triethylamine in order to accelerate the reaction. Such an amine-based catalyst can be used as it is also as a polymerization catalyst for a polyimide precursor resin.

<Direct Method>

First, the method which can be preferably used to produce a polyamic acid and which has been described in the above-mentioned section "1) Polyamic Acid" (method for carrying out the step (I)) is carried out, and the reaction liquid obtained after the reaction is directly prepared as a polyamic acid solution. Thereafter, the obtained polyamic acid solution is mixed with a silylating agent. When the solution is stirred in the range of 0 to 120° C. (preferably 5 to 80° C.) for 1 to 72 hours, it is possible to obtain a polyimide precursor resin composed of the polyamic acid silyl ester (direct method). Note that, in the case of reaction at a stirring temperature of 80° C. or above, the molecular weight is likely to vary depending on the temperature history during polymerization, and imidization may be caused by heat. Thus, it tends to be difficult to stably produce the polyimide precursor resin. As a silylating agent which can be used in the direct method, it is preferable to use a silylating agent which does not contain chlorine atoms because it is unnecessary to purify the silylated polyamic acid or the obtained polyimide. The silylating agent which does not contain chlorine atoms includes N,O-bis(trimethylsilyl)trifluoroacetamide, N,O-bis(trimethylsilyl)acetamide, and hexamethyldisilazane. In addition, the silylating agent is particularly preferably N,O-bis(trimethylsilyl)acetamide and hexamethyldisilazane because they do not contain fluorine atoms and are inexpensive.

All of the methods of producing the polyimide precursor resin of the present invention described above can be carried out in an organic solvent. When the polyimide precursor resin is produced in an organic solvent as described above, it is possible to easily obtain the polyimide precursor resin solution of the present invention (varnish of polyimide precursor resin).

Hereinabove, the method which can be preferably used to produce the polyimide and the polyimide precursor resin of the present invention has been described. Next, the polyimide precursor resin solution of present invention is described.

[Polyimide Precursor Resin Solution]

A polyimide precursor resin solution of the present invention comprises the polyimide precursor resin (preferably, the polyamic acid) of the present invention and an organic solvent.

As the organic solvent used for the polyimide precursor resin solution (resin solution: varnish), it is possible to preferably use one same as the above-described polymerization solvent. Thus, the polyimide precursor resin solution (preferably the polyamic acid solution) of the present invention may be prepared by carrying out the method for producing the polyimide precursor resin of the invention described above (for example, when the polyimide precursor resin is a polyamic acid, a method which can be preferably used to produce a polyamic acid (method for carrying out the step (Ia)), and using the reaction liquid obtained after the reaction as it is as a polyimide precursor resin solution (for example, when the polyimide precursor resin is a polyamic acid, a polyamic acid solution).

The content of the polyimide precursor resin (preferably polyamic acid) in the polyimide precursor resin solution (preferably polyamic acid solution) is not particularly limited, but is preferably 1 to 80% by mass and more preferably 5 to 50% by mass. If the content is less than the lower limit, the production of the polyimide film tends to be difficult. Meanwhile, if the content exceeds the upper limit, the production of the polyimide film tends to be difficult as well. Note that the polyimide precursor resin solution (preferably polyamic acid solution) can be preferably used for producing the polyimide of the present invention, and can be preferably used to produce polyimides of various shapes. For example, it is possible to easily produce a polyimide in the shape of a film by applying the polyimide precursor resin solution (preferably polyamic acid solution) on various substrates, followed by imidization and subsequent curing.

Hereinabove, the polyimide precursor resin solution of the present invention has been described. Next, the polyimide solution of the present invention is described.

[Polyimide Solution]

A polyimide solution of the present invention comprises the polyimide of the present invention and an organic solvent.

As the organic solvent used for the polyimide solution, it is possible to preferably use one same as the above-described polymerization solvent. In addition, as the polyimide solution of the present invention, when a polyimide obtained by carrying out the method for producing the polyimide of the present invention described above is sufficiently soluble in the polymerization solvent (organic solvent) used in the production, the reaction liquid obtained after the reaction may be used as it is as a polyimide solution (for example, the reaction liquid obtained after the reaction can be used as it is as a polyimide solution by using an organic solvent (polymerization solvent) which can sufficiently dissolve the obtained polyimide and forming a polyimide in the solvent).

As described above, as the organic solvent used for the polyimide solution of the present invention, it is possible to preferably use one same as the above-described polymerization solvent. Note that, as the organic solvent used for the polyimide solution of the present invention, it is possible to use, for example, a halogen-based solvent having a boiling point of 200° C. or below (such as dichloromethane (boiling point 40° C.), trichloromethane (boiling point 62° C.), carbon tetrachloride (boiling point 77° C.), dichloroethane (boiling point 84° C.), trichloroethylene (boiling point 87° C.), tetrachloroethylene (boiling point 121° C.), tetrachloroethane (boiling point 147° C.), chlorobenzene (boiling point 131° C.), or o-dichlorobenzene (boiling point 180° C.)) from the viewpoint of evaporation and removability of the solvent when the polyimide solution is used as a coating liquid.

In addition, from the viewpoints of solubility, film formation, productivity, industrial availability, presence or absence of existing equipment, and price, the organic solvent used for the polyimide solution is preferably N-methyl-2-pyrrolidone, N,N-dimethylformamide, N,N-dimethylacetamide, γ-butyrolactone, propylene carbonate, tetramethylurea, 1,3-dimethyl-2-imidazolidinone, and cyclopentanone, more preferably N-methyl-2-pyrrolidone, N,N-dimethylacetamide, γ-butyrolactone, and tetramethylurea, and particularly preferably N,N-dimethylacetamide and γ-butyrolactone. Note that one of those organic solvents may be used alone or two or more thereof may be used in combination.

In addition, the polyimide solution can also be preferably used as a coating liquid and the like for producing various processed products. For example, in the case of forming a film, a polyimide film may be formed when the polyimide solution of the present invention is used as a coating liquid and applied on a base material to obtain a coating film, and then the solvent is removed. The coating method is not particularly limited, and it is possible to appropriately use known methods (such as the spin coating method, the bar coating method, and the dip coating method).

In the polyimide solution, the content (dissolution amount) of the polyimide is not particularly limited, but is preferably 1 to 75% by mass and more preferably 10 to 50% by mass. If the content is less than the lower limit, the film thickness after film formation tends to be thin in the case of use for film formation or the like. Meanwhile, if the content exceeds the upper limit, a portion thereof tends to be insoluble in the solvent. Moreover, depending on the use purpose and the like, the polyimide solution may be further added with an additive such as an antioxidant (phenol-based, phosphate-based, thioether-based, or the like), an ultraviolet absorber, a hindered amine-based light stabilizer, a nucleating agent, a resin additive (filler, talc, glass fiber, or the like), a flame retardant, a processability improver, or a lubricant. Note that these additives are not particularly limited. Known additives can be appropriately used, and commercially available additives may be used.

EXAMPLES

Hereinafter, the present invention is more specifically described based on Examples and Comparative Examples, but the present invention is not limited to the following examples.

First, description is provided for the method for evaluating the characteristics of the compounds and polyimides obtained in the following examples and the like.

<IR Measurement and NMR Measurement>

The measuring apparatuses used in the IR measurement and NMR measurement employed in the examples and the comparative examples were an IR measuring apparatus (FT/IR-4100 manufactured by JASCO Corporation) and an NMR measuring apparatus (manufactured by VARIAN under the trade name: UNITY INOVA-600), respectively.

<Measurement of Total Luminous Transmittance>

The value of the total luminous transmittance of the polyimide (unit: %) was determined by using the polyimide obtained in each example and the like (polyimide in the shape of a film) as it is as a sample for measurement, using a measuring apparatus manufactured by NIPPON DENSHOKU INDUSTRIES CO., LTD. under the trade name "Haze meter NDH-5000," and carrying out measurement in accordance with to JIS K7361-1 (issued in 1997).

<Measurement of 5% Weight Loss Temperature (Td5%)>

The 5% weight loss temperature of the polyimide was determined by preparing 2 to 4 mg of sample from the polyimide obtained in each example and the like, placing the sample in an aluminum sample pan, using a thermogravimetric analyzer (manufactured by SII NanoTechnology Inc. under the trade name of "TG/DTA7200") as a measuring apparatus to set the scan temperature from 30° C. to 550° C. under a nitrogen gas atmosphere, heating under the condition of a rate of temperature rise of 10° C./min, and measuring the temperature at which the weight loss of the sample used reached 5%.

<Evaluation of Solubility>

A sample in the shape of a film in an amount of 100 mg was prepared from the polyimide obtained in each example and the like, and the sample was added to 900 mg of N-methyl-2-pyrrolidone (NMP) introduced in advance into a capped sample bottle (volume 5 ml). The sample was added to NMP as described above, and then the time of complete dissolution of the sample in NMP was measured under the conditions of atmospheric pressure and room temperature (25° C.) to evaluate the solubility in accordance with the following criteria A to F.

<Evaluation Criteria>

A: The entire amount of the sample dissolved within 6 hours.
B: The entire amount of the sample dissolved within 12 hours.
C: The entire amount of the sample dissolved within 24 hours.
D: The entire amount of the sample dissolved within 1 week.
E: It took 1 week or longer for the entire amount of the sample to dissolve.
F: The sample swelled and did not always sufficiently dissolve.
G: The sample was insoluble.

Example 1

<Step of Preparing Raw Material Compound>

The method same as the method disclosed in Example 1 of JP 2015-137235 A was employed to prepare a compound represented by the following formula (A):

[Chem. 16]

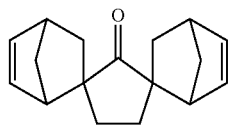

(A)

(5-norbornene-2-spiro-α-cyclopentanone-α'-spiro-2"-5"-norbornene). Hereinafter, the compound represented by the formula (A) is simply referred to as a "raw material compound" for convenience.

<Step of Preparing Tetracarboxylic Acid Tetramethyl Ester>

A 1000 mL autoclave vessel (manufactured by Taiatsu Techno Corporation under the trade name of "Hyper Gras Star TEM-V-type") made of glass was added with methanol (820 mL), $CuCl_2(II)$ (81.6 g, 454 mmol), the raw material compound (35.6 g, 148 mmol), and $Pd_3(OAc)_5(NO_2)$ (166 mg, 0.74 mmol in terms of Pd), to thereby obtain a mixture liquid. Note that $Pd_3(OAc)_5(NO_2)$ was produced by employing a method described in page 1991 of Dalton Trans (vol. 11), issued in 2005.

Subsequently, a glass tube was provided so that bubbling of gas could be performed through the glass tube to the mixture liquid present inside the vessel. After that, the vessel was tightly closed and the inside atmospheric gas was substituted with nitrogen. After that, a vacuum pump was connected to the vessel to reduce the pressure inside the vessel (pressure inside the vessel: 0.015 MPa). Next, the mixture liquid was stirred for 5 hours while supplying, by bubbling, carbon monoxide at a rate (flow rate) of 0.015 mole equivalents/min relative to the raw material compound through the glass tube into the mixture liquid and maintaining the temperature at 25 to 30° C. and pressure in the vessel at 0.13 MPa. After that, the mixture liquid was further stirred for 3 hours while maintaining the pressure in the vessel at 0.13 MPa under the temperature condition of 40° C. Thereby, the reaction liquid was obtained. Subsequently, the atmospheric gas containing carbon monoxide was removed from the inside of the vessel. Then, methanol was removed (removed by distillation) from the reaction liquid by concentrating the reaction liquid with an evaporator. Thereby, the reaction product was obtained (yield amount 65.4 g, yield rate 92.6%, polymerization product 0.90%: the yield amount and the yield rate are values determined by measurement by high performance liquid chromatography (HPLC, manufactured by Agilent, the 1200 Series) analysis after metal salt is removed from a small amount sampled from the reaction product, and the ratio of polymerization product is a value determined by measurement by GPC analysis).

Thereafter, the reaction product was transferred to another vessel (a 2000 mL-volume glass container having a stirring function). The reaction product was added with toluene (1200 mL) and vigorously stirred at a temperature condition of 80° C. for 1 hour. Thus, the reaction product was extracted by toluene to obtain a toluene extraction liquid (concentration of the reaction product: 8.4% by mass). Subsequently, while maintaining the temperature of the toluene extraction liquid at 80° C., toluene-insoluble CuCl and $Pd_3(OAc)_5$ $(NO_2)$ were separated from the toluene extraction liquid by vacuum filtration using a Kiriyama funnel.

Next, after separating CuCl and $Pd_3(OAc)_5(NO_2)$ as described above, the toluene extraction liquid (filtrate) was washed twice with 5% by mass of hydrochloric acid (400 ml) at a temperature condition of 80° C. Subsequently, the toluene extraction liquid thus washed with hydrochloric acid was washed once with saturated aqueous solution of sodium hydrogen carbonate (400 ml) at a temperature condition of 80° C. Next, the toluene extraction liquid obtained after washing was filtered with a filter to obtain a toluene extraction liquid (hereinafter, the toluene extraction liquid obtained after the filter filtration is referred to as the "toluene extraction liquid (A)" in some cases). Note that the concentration of the reaction product in the toluene extraction liquid (A) was 7.9% by mass. Subsequently, the toluene extraction liquid (A) after the filter filtration was concentrated by heating to about 110° C., the boiling point of toluene under normal pressure (0.1 MPa). Toluene in a total amount of 900 ml was removed by distillation by the concentration operation to obtain a liquid concentrate in which the concentration of the reaction product was adjusted to 20% by mass (liquid concentrate of the toluene extraction liquid). After that, the liquid concentrate was allowed to cool at room temperature (25° C.) for about 12 hours to precipitate white crystals.

Subsequently, white crystals were separated by filtration from the liquid concentrate in which white crystals were precipitated, and the filtrate was collected. Moreover, the white crystals separated by filtration were subjected to rinse washing twice with 50 mL of toluene, and the rinse washing liquid was collected. Next, the filtrate and the rinse washing liquid were mixed, and then the mixture liquid was concentrated with an evaporator. A brown viscous liquid was obtained by the concentration step. Subsequently, the obtained viscous liquid was depressurized under the conditions of reduced pressure (pressure: 0.5 mmHg) at 80° C. the whole day to remove (dry) the solvent, and thus a product A composed of brown solid (35.3 g, yield rate 50%) was obtained.

Figure 2:
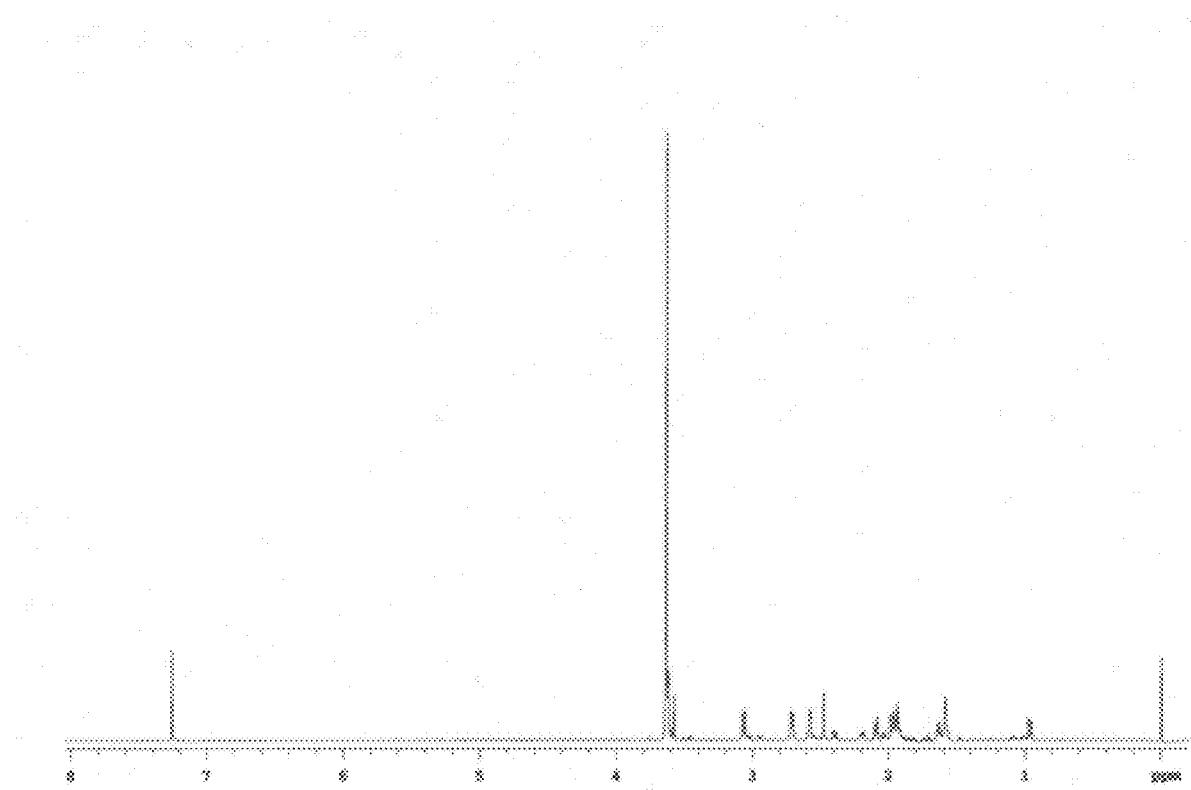
FIG. 2 is a graph showing a $^1$H-NMR (CDCl$_3$) spectrum of the tetracarboxylic acid tetramethyl ester (intermediate) obtained in Example 1.

To identify the structure of the thus obtained product A, IR measurement and NMR ($^1$H-NMR) measurement were carried out. FIG. 1 shows an IR spectrum of the thus obtained product A, and FIG. 2 shows a $^1$H-NMR ($CDCl_3$) spectrum thereof. As is apparent from the results shown in FIG. 1 and FIG. 2, the obtained product A was identified to be a compound represented by the following formula (B):

[Chem. 17]

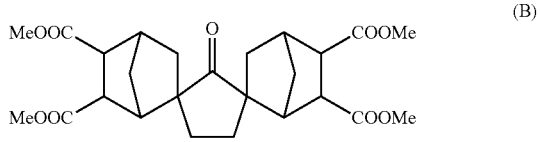

(B)

(norbornane-2-spiro-α-cyclopentanone-α'-spiro-2"-norbornane-5,5",6,6"-tetracarboxylic acid tetramethyl ester). Moreover, when a GPC analysis was conducted on the obtained product A, the content of polymerization products being impurities (a polymerization product in which norbornene rings in the raw material compound are addition-polymerized, a mixture of polymerization products in which multiple norbornene rings are bonded at keto groups, and the like) was identified to be 0.7% by mass.

Figure 3:
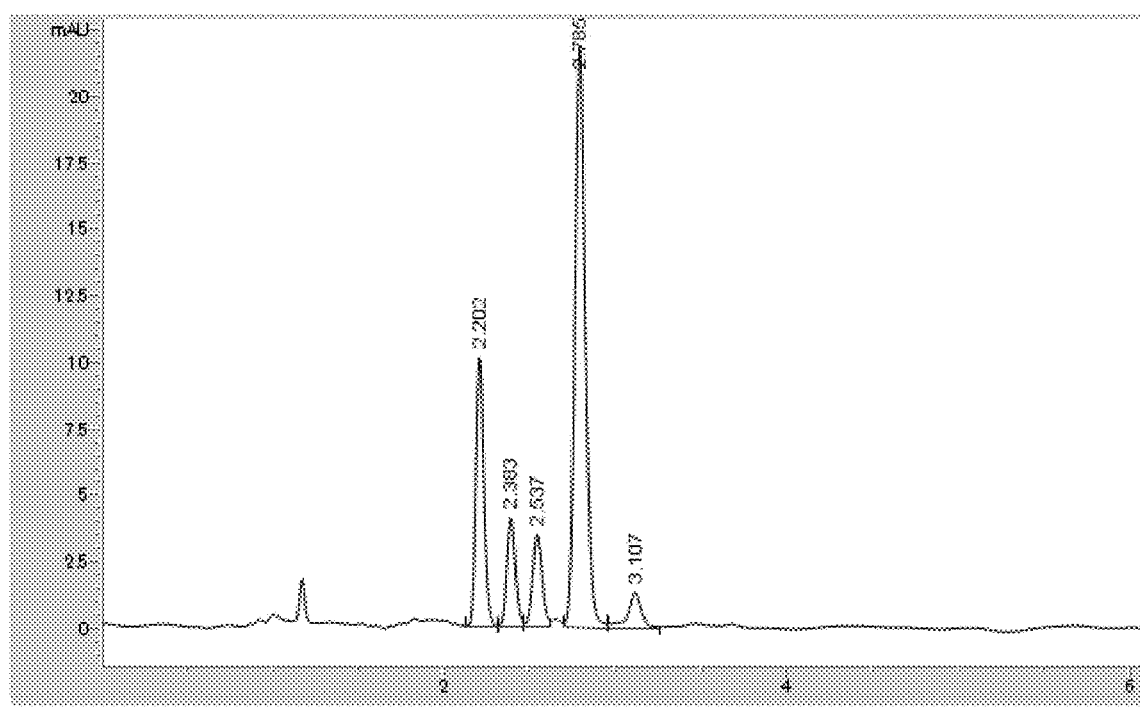
FIG. 3 is a chromatogram determined by HPLC measurement of the tetracarboxylic acid tetramethyl ester (intermediate) obtained in Example 1.

In addition, HPLC measurement was carried out on the obtained product A (the product A could not be detected by GC measurement and thus was judged as a low volatile substance in terms of molecular weight, and HPLC measurement was carried out instead of GC measurement) The HPLC measurement was carried out as follows. Specifically, a measuring apparatus manufactured by Agilent Technologies, Inc. under the trade name of "1200 Series" was used, and a column manufactured by Agilent Technologies, Inc. under the trade name of "Eclipse XDB-C18 (5 μm, diameter: 4.6 mm, length: 150 mm)" was used. The solvent used was a mixture of acetonitrile and distilled water (acetonitrile/distilled water=70 ml/30 ml). The solvent flow rate was set to 1 ml/min, the detection wavelength of a diode array detector (DAD) was set to 210 nm, and the temperature thereof was set to 35° C. In addition, a sample was prepared by adding 1 mg of the product A per 1.5 ml of the solvent. In addition, the summed amount (content ratio) of the trans-exo-endo isomer and the cis-exo-endo isomer, and the content of the trans-exo-endo isomer were confirmed by calculation using a calibration curve from the area ratio of HPLC (standard sample:dicyclopentadiene). FIG. 3 shows the results of the HPLC measurement.

As is apparent from the results of the HPLC measurement shown in FIG. 3, the product A (norbornane-2-spiro-α-cyclopentanone-α'-spiro-2"-norbornane-5,5",6,6"-tetracarboxylic acid tetramethyl ester) was found to be a mixture of multiple isomers. Note that, in the chromatogram chart (HPLC) shown in FIG. 3, the peak at the position of about 3.1 minutes on the horizontal axis is a toluene peak, and the peak at about 1.2 minutes on the horizontal axis is solvent shock. From the area ratio of the chromatogram, the product A (mixture of multiple isomers) was found to be such that the summed amount (content ratio) of the trans-exo-endo isomer and the cis-exo-endo isomer was 50% by mole or more relative to the total amount of all isomers, and the content of the trans-exo-endo isomer was 30% by mole or more relative to the total amount of all isomers.

<Step of Preparing Tetracarboxylic Dianhydride>

First, into a flask of volume 300 mL with a refluxing tube, a solution formed by dissolving 48 g of the product A (compound represented by the formula (B), molecular weight 476.52) in 192 g of acetic acid was added, and then 0.38 g of trifluoromethanesulfonic acid (TfOH, boiling point: 162° C.) as a homogeneous acid catalyst was added into the solution, to thereby obtain a solution for reaction. Note that, in the solution for reaction, the mole ratio of the product A to the functional groups of the catalyst ([amount of moles of the product A]:[amount of moles of the functional groups (sulfonic acid) in the catalyst]) was 1:0.025.

Next, after the atmospheric gas in the flask was substituted with nitrogen, the solution for reaction was heated while being stirred using a magnetic stirrer under a nitrogen stream and under a condition of atmospheric pressure. The temperature inside the flask was set to 118° C. by the heating, and refluxing was carried out for 0.5 hours (refluxing step). After the refluxing step, a step (hereinafter referred to as "step (i)") was carried out in which vapor generated by using a Liebig condenser was removed by distillation under the heating condition of 118° C. and at the same time the amount of liquid in the flask was kept constant by adding acetic acid into the flask by using a dropping funnel. Note that in step (i), 2 hours after the removal by distillation of the vapor was started, a grayish white precipitate produced was observed in the liquid inside the flask (in the reaction solution). In addition, in step (i), the progress of the reaction was checked every hour by analyzing the distillate removed by distillation to the outside of the system by means of mass measurement and a gas chromatograph. Note that the analysis revealed that acetic acid, methyl acetate, and water were present in the distillate. In addition, when the removal speed of the distillate in the above step was measured, the speed (rate) of removing the distillate was about 35 mL per 1 hour. In step (i), since the distillation of the methyl acetate was stopped 8 hours after the removal by distillation of the vapor was started, the heating was stopped and step (i) was finished. Note that the amount of the methyl acetate distillated (amount collected, excluding the amount dissipated) by the time 8 hours had passed since the removal by distillation was started was 26.4 g (88%). In addition, the amount of the acetic acid removed by distillation by the time the distillation of the methyl acetate was stopped (by the time the reaction was finished) was 170 g. The step (i) was carried out as described above, and after standing at room temperature the whole day, vacuum filtration using filter paper was carried out to obtain a grayish white solid content. Then, a washing and drying step was carried out including washing (rinse-washing) the obtained grayish white solid content five times with ethyl acetate (30 mL) cooled to −10° C. and drying the solid content under reduced pressure overnight (15 hours) at 80° C. Thereby, a product B composed of 31.0 g of grayish white powder was obtained. To identify the structure of the thus obtained product B, IR measurement, NMR ($^1$H-NMR) measurement, and HPLC measurement were carried out. Note that the HPLC measurement employed was the same method as the measurement method carried out on the product A except that naphthalene was used as the standard sample for the calibration curve.

Figure 4:
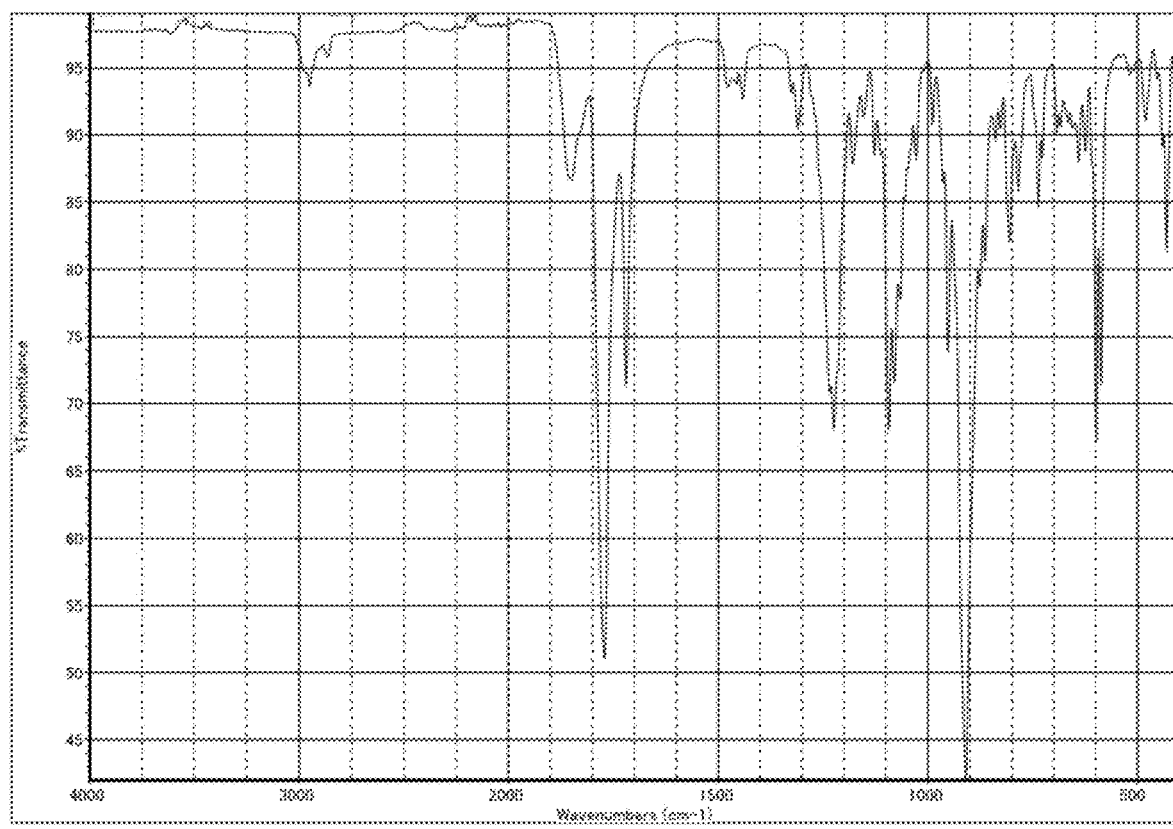
FIG. 4 is a graph showing an IR spectrum of a tetracarboxylic dianhydride obtained in Example 1.
Figure 5:
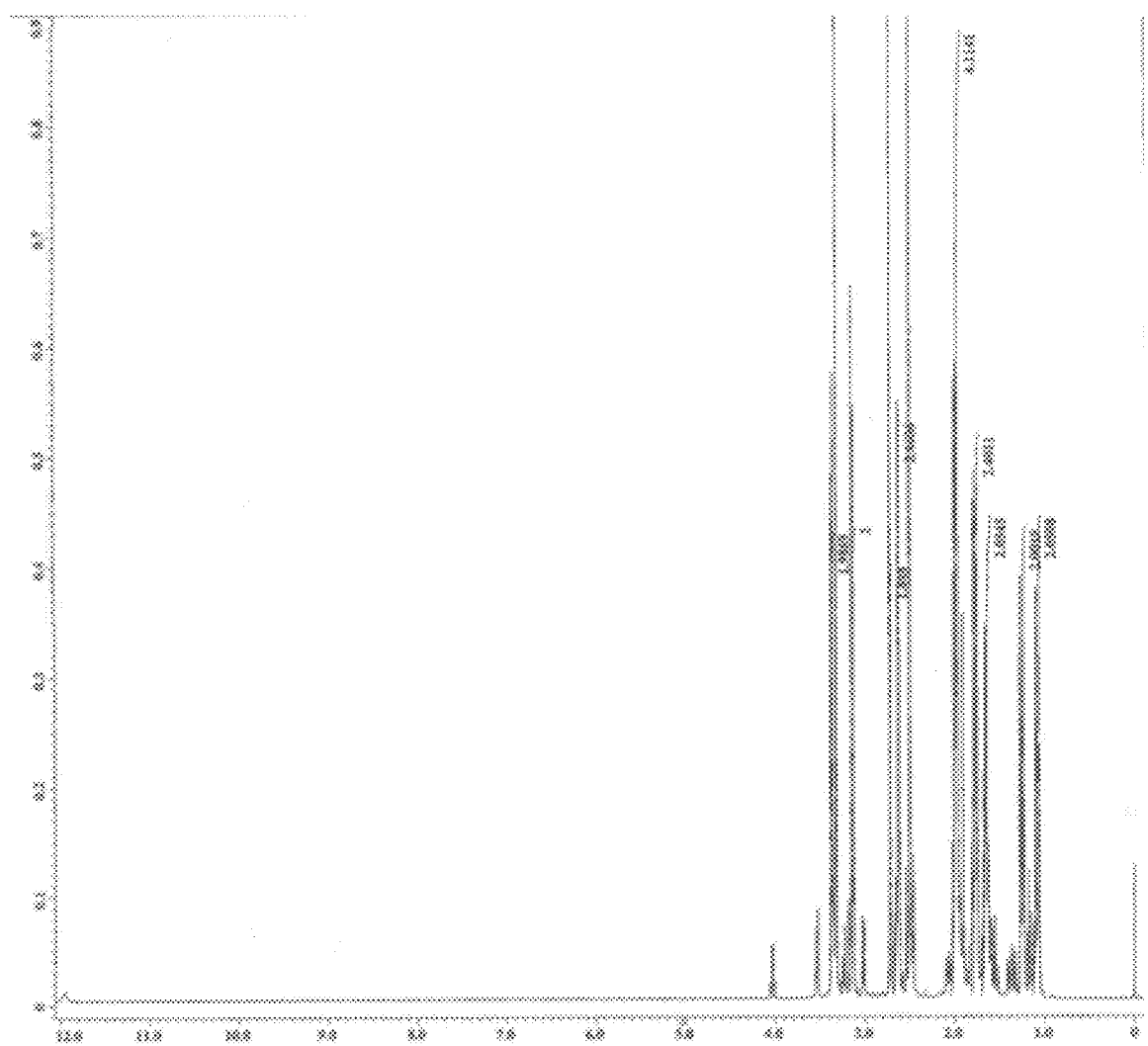
FIG. 5 is a graph showing a $^1$H-NMR (CDCl$_3$) spectrum of the tetracarboxylic dianhydride obtained in Example 1.
Figure 6:
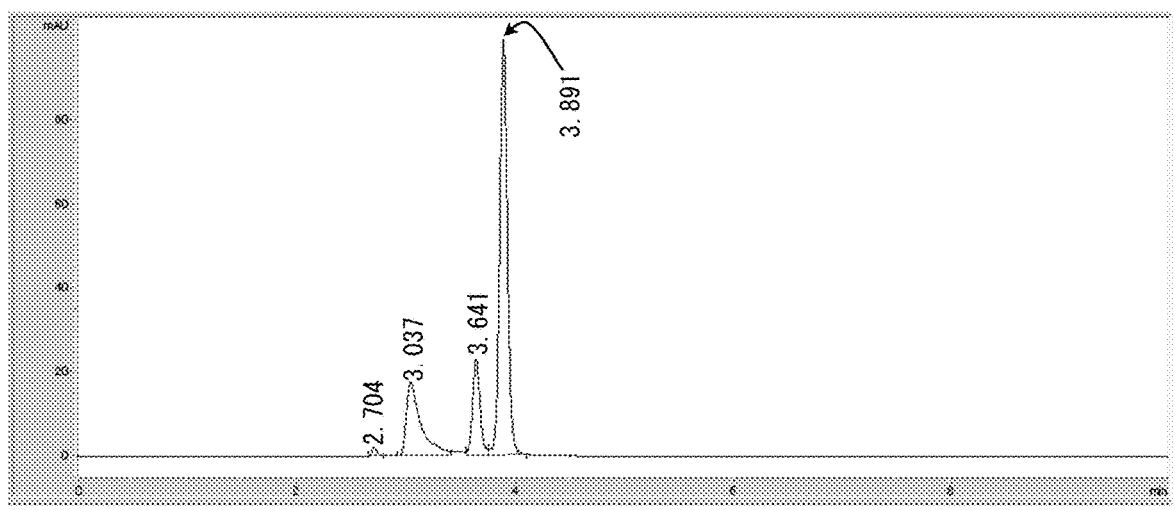
FIG. 6 is a chromatogram determined by HPLC measurement of the tetracarboxylic dianhydride obtained in Example 1.

FIG. 4 shows an IR spectrum of the thus obtained product B, and FIG. 5 shows a $^1$H-NMR (CDCl$_3$) spectrum thereof. In addition, FIG. 6 shows the results of the HPLC measurement. As is apparent from the results shown in FIG. 4 to FIG. 6, the obtained product B was identified to be a compound represented by the following formula (C):

[Chem. 18]

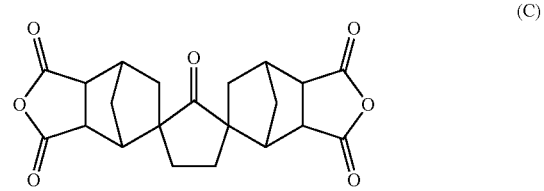

(C)

(norbornane-2-spiro-α-cyclopentanone-α'-spiro-2"-norbornane-5,5",6,6"-tetracarboxylic dianhydride: CpODA). In addition, as is apparent from the measurement results of HPLC shown in FIG. 6, the product B was found to be a mixture of multiple isomers (the signal at 2.7 minutes is an unknown peak). As described above, the product B was found to be an isomeric mixture of CpODA. Note that, regarding the compound (acid dianhydride) thus obtained, the yield rate of the product relative to the theoretical amount, calculated from the prepared amount of the raw material compound used, was determined, and the yield rate was found to be 80%.

<Measurement by Gas Chromatography>

Figure 7:
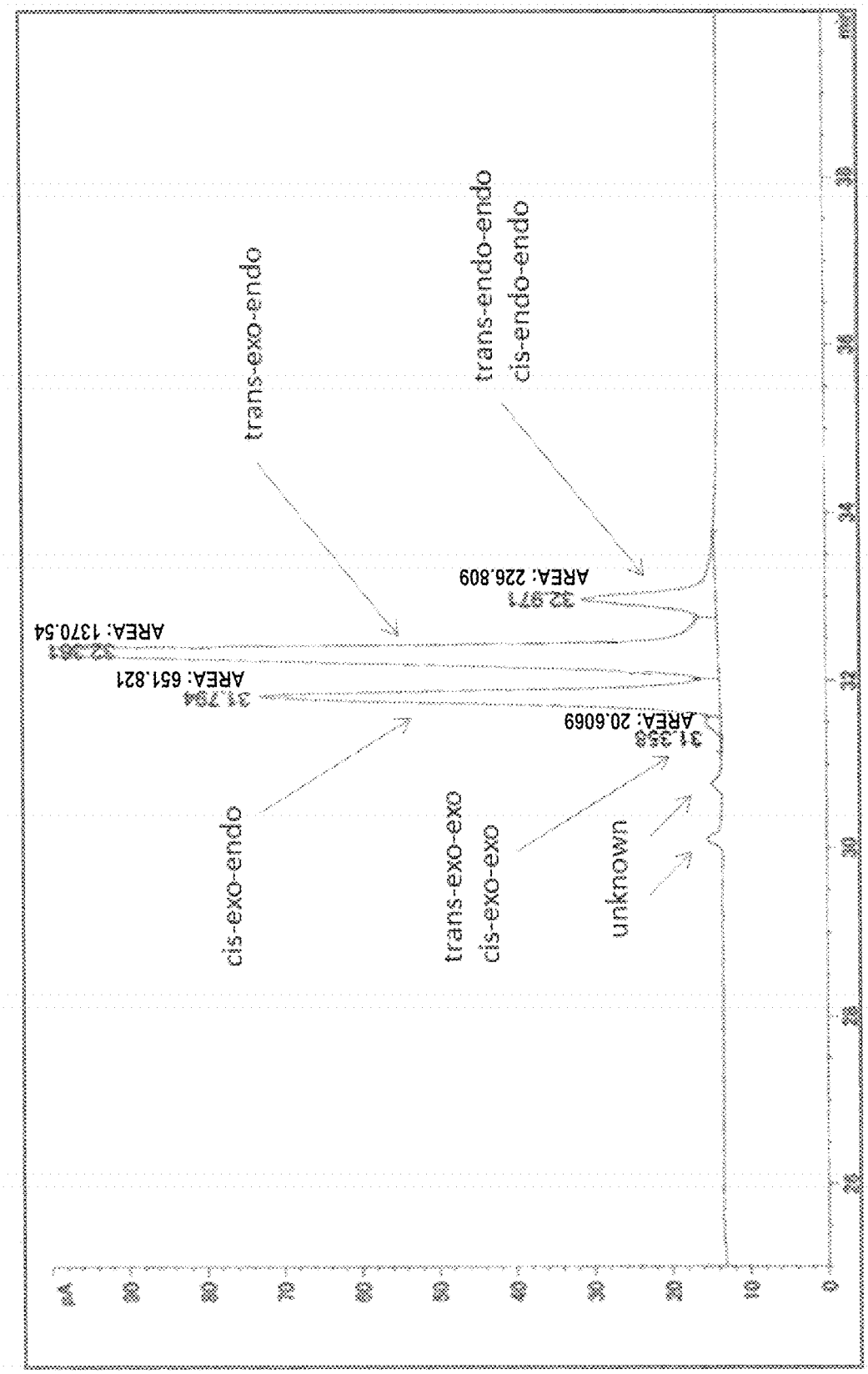
FIG. 7 is a chromatogram determined by gas chromatography measurement (GC analysis) of the tetracarboxylic dianhydride obtained in Example 1.

A portion of the product B thus obtained (grayish white powder) was collected to carry out measurement by gas chromatography (GC measurement and GC-MS measurement). In the measurement, a dimethylacetamide solution (hereinafter simply referred to as the "DMAc solution"), containing the product B as a measurement sample at a ratio of 0.1% by mass, was prepared. A gas chromatograph mass spectrometer (manufactured by Agilent under the trade name of "7890A") was used as a measuring apparatus. Helium was used as a mobile phase gas (carrier gas). RESTEX Rtx-5 Amine (30 m) was used as a stationary phase (column). The trade name "G4513A" manufactured by Agilent was used as an MS detector. G4513A manufactured by Agilent was used as an injector. The DMAc solution being the measurement sample in an amount of 1 μL was injected with the injector. The flow rate of the helium being a carrier gas was set to 10 mL/min (constant). The temperature conditions was set to the conditions that, after retaining at 50° C. (initial temperature) for 1 minute, the temperature was raised from 50° C. to 300° C. with a rate of temperature rise of 10° C./min, and was retained at 300° C. for 25 minutes. In this way, GC measurement and GC-MS measurement were carried out, and thereby the chromatogram (separation image) of the product B was determined. After that, the area of each of the peaks in the chromatogram was determined, and the content ratio of the isomer derived from each peak was calculated based on the ratio of the area of each peak relative to the sum of areas (total area). Thus, the content ratio of each isomer was determined. FIG. 7 shows the chromatogram (separation image) of the product B as the obtained results.

Note that, in the chromatogram shown in FIG. 7, 4 types of peaks were confirmed from the obtained product B (grayish white powder), and their GC-MS measurement showed that the isotope ion peak (M+1) was 385 (acid dianhydride: molecular weight 384.38). Thus, the product B was found to contain isomers of the same molecular weight. In addition, from the area ratio of each peak of the gas chromatogram shown in FIG. 7, it was found that the content of the trans-exo-endo isomer was 60.4% by mole, the content of the cis-exo-endo isomer was 28.7% by mole, the summed amount of the cis-exo-exo isomer and the trans-exo-exo isomer was 0.9% by mole, and the summed amount of the trans-endo-endo isomer and the cis-endo-endo isomer was 10.0% by mole (note that the content ratio (% by mole) is a ratio to the total amount of the CpODA stereoisomers). As described above, the product B was found to be the compound represented by the formula (C) and was found to be a mixture of isomers in which the summed amount of the trans-exo-endo isomer and the cis-exo-endo isomer was 89.1% by mole and the content of the trans-exo-endo isomer was 60.4% by mole. Table 1 presents the obtained results. Note that the structures of the six stereoisomers of the compound represented by the formula (C) are represented below.

[Chem. 19]

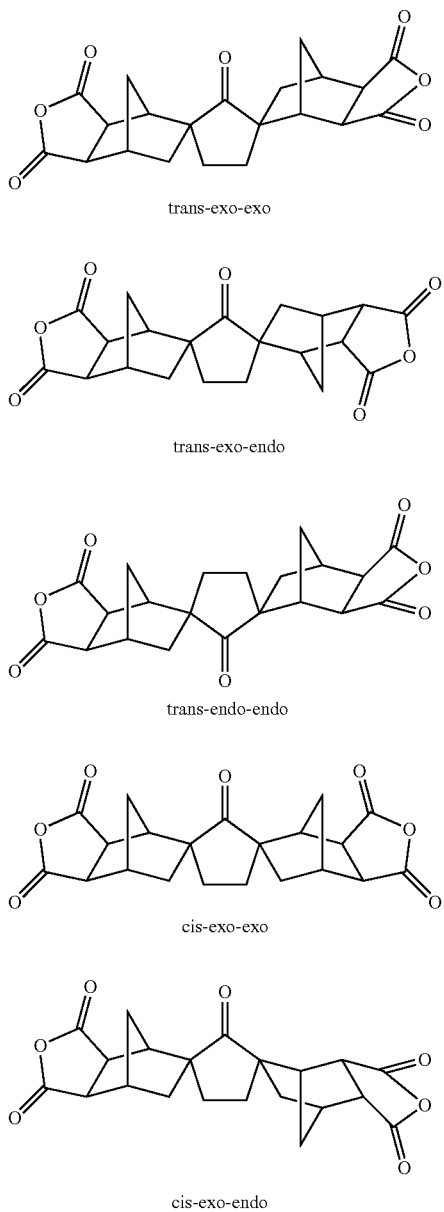

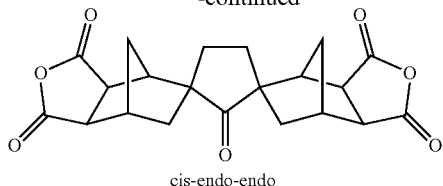

cis-endo-endo

Example 2

A product C (CpODA) was prepared in the same manner as that of Example 1 except that the washing and drying step employed in the step of preparing a tetracarboxylic dianhydride was changed as follows. Specifically, the product C composed of 25.1 g of grayish white was obtained (yield rate 65%) in the same manner as that of in Example 1 except that, in the step of preparing a tetracarboxylic dianhydride, the washing and drying step carried out on the obtained grayish white solid content was changed from the step of washing (rinse-washing) five times with ethyl acetate (30 mL) cooled to −10° C. and drying under reduced pressure overnight (15 hours) at 80° C. to the step of washing (rinse-washing) once with 30 ml of acetic acid (20° C.), followed by washing (rinse-washing) five times with 30 ml of ethyl acetate (20° C.) and drying under reduced pressure overnight (15 hours) at 80° C. To identify the structure of the thus obtained product C, IR measurement and NMR ($^1$H-NMR) measurement were carried out. As a result, the obtained product C was found to be the compound represented by the formula (C) (CpODA).

In addition, when the obtained product C was measured by gas chromatography in the same manner as that of Example 1, it was found that, from the area ratio of each peak of the gas chromatogram, the content of the trans-exo-endo isomer was 69.4% by mole, the content of the cis-exo-endo isomer was 13.7% by mole, the summed amount of the cis-exo-exo isomer and the trans-exo-exo isomer was 0.2% by mole, and the summed amount of the trans-endo-endo isomer and the cis-endo-endo isomer was 16.7% by mole. As described above, the product C was found to be the compound represented by the formula (C) (CpODA) and was found to be a mixture of isomers in which the summed amount of the trans-exo-endo isomer and the cis-exo-endo isomer was 83.1% by mole and the content of the trans-exo-endo isomer was 69.4% by mole (note that the content ratio (% by mole) is a ratio to the total amount of the CpODA stereoisomers). The comparison of the results of such measurement with the results obtained in Example 1 showed that it is possible to change the ratios of CpODA isomers also by the difference in the washing and drying step after preparation of CpODA.

Comparative Example 1

The same method as the method disclosed in Example 1 of JP 2015-137235 A was employed to prepare a raw material compound composed of the compound represented by the formula (A). The raw material compound was subjected to the same step as the steps described in Examples 1 and 2 of WO 2011/099518 A to obtain a product D, the compound represented by the formula (C) (tetracarboxylic dianhydride). Specifically, the product D was obtained by employing the same step as the steps described in Examples 1 and 2 of WO 2011/099518 A except that the raw material compound was used as 5-norbornene-2-spiro-α-cyclopentanone-α'-spiro-2"-5"-norbornene.

Note that, when the obtained product D was measured by gas chromatography in the same manner as that of Example 1, it was found that, from the area ratio of each peak of the gas chromatogram, the content of the trans-exo-endo isomer was 25.2% by mole, the content of the cis-exo-endo isomer was 16.3% by mole, the summed amount of the cis-exo-exo isomer and the trans-exo-exo isomer was 0.7% by mole, and the summed amount of the trans-endo-endo isomer and the cis-endo-endo isomer was 57.8% by mole (note that the content ratio (% by mole) is a ratio to the total amount of the CpODA stereoisomers). As described above, the product D was an isomeric mixture of CpODA. Table 1 presents the obtained results.

Comparative Example 2

The same method as the method disclosed in Example 1 of JP 2015-137235 A was employed to prepare a raw material compound composed of the compound represented by the formula (A). The raw material compound was subjected to the same step as the step described in the monomer synthesis step described in Synthetic Example 2 and Example 1 of WO 2014/034760 A to obtain a product E, the compound represented by the formula (C) (tetracarboxylic dianhydride). Specifically, the product E was obtained by employing the same step as the step described in the monomer synthesis step described in Synthetic Example 2 and Example 1 of WO 2014/034760 A except that the raw material compound was used as 5-norbornene-2-spiro-α-cyclopentanone-α'-spiro-2"-5"-norbornene.

Note that, when the obtained product E was measured by gas chromatography in the same manner as that of Example 1, it was found that, from the area ratio of each peak of the gas chromatogram, the content of the trans-exo-endo isomer was 1.4% by mole, the content of the cis-exo-endo isomer was 1.0% by mole, the summed amount of the cis-exo-exo isomer and the trans-exo-exo isomer was 0.3% by mole, and the summed amount of the trans-endo-endo isomer and the cis-endo-endo isomer was 97.3% by mole (note that the content ratio (% by mole) is a ratio to the total amount of the CpODA stereoisomers). As described above, the product E was an isomeric mixture of CpODA. Table 1 presents the obtained results.

Example 3

First, under a nitrogen atmosphere, a 100 mL three-necked flask having a stirrer and a reflux condensing tube (Dimroth) was introduced with 2.123 g (10 mmol) of 2,2'-dimethylbiphenyl-4,4'-diamine (m-tol: meta-toluidine) as an aromatic diamine and introduced with 3.8438 g (10 mmol) of the product B (isomeric mixture of CpODA obtained in Example 1) as a tetracarboxylic dianhydride, to thereby introduce an aromatic diamine and the tetracarboxylic dianhydride into the three-necked flask.

Next, the three-necked flask was introduce with 2.784 g of dimethylacetamide (N,N-dimethylacetamide) and 11.138 g of γ-butyrolactone as organic solvents and was introduced with 50 mg (0.5 mmol) of triethylamine being a reaction accelerator, to thereby obtain a mixture liquid formed by mixing the aromatic diamine (m-tol), the tetracarboxylic dianhydride (the product B), the organic solvents (N,N-dimethylacetamide and γ-butyrolactone), and a reaction accelerator (triethylamine).

Subsequently, the mixture liquid thus obtained was stirred while being heated under a nitrogen atmosphere at a temperature condition of 180° C. for 3 hours, to thereby obtain a viscous uniform pale yellow reaction liquid (polyimide solution). As described above, a polyimide derived from the aromatic diamine (m-tol) and the tetracarboxylic dianhydride (the product B) was prepared by a heating step, to thereby obtain a reaction liquid (polyimide solution). Here, it is apparent that, by such heating, the reaction of the aromatic diamine with the tetracarboxylic dianhydride first proceeded to form a polyamic acid, and then imidization proceeded to form a polyimide. When the polyimide solution thus obtained was used to measure the intrinsic viscosity [η] of the polyimide, the intrinsic viscosity [η] of the polyimide was 0.43 dL/g.

Next, the reaction liquid was spin-coated on a glass plate (length: 75 mm, width 50 mm, thickness 1.3 mm) to form a coating film on the glass plate. After that, the glass substrate having the coating film formed thereon was placed on a hot plate of 60° C. and was allowed to stand for 2 hours. Thereby, the solvent was vaporized and removed from the coating film. After the solvent removal treatment, the glass substrate having the coating film formed thereon was introduced into an inert oven in which nitrogen was flowing at a

TABLE 1

|  | Example 1 | Example 2 | Comparative Example 1 | Comparative Example 2 |
|---|---|---|---|---|
| Tetracarboxylic Dianhydride (CpODA) | Product B (Unit: % by Mole) | Product C (Unit: % by Mole) | Product D (Unit: % by Mole) | Product E (Unit: % by Mole) |
| Content of Trans-Exo-Endo Isomer (Peak at Retention Time of Around 32.4 Minutes) | 60.4 | 69.4 | 25.2 | 1.4 |
| Content of Cis-Exo-Endo Isomer (Peak at Retention Time of Around 31.8 Minutes) | 28.7 | 13.7 | 16.3 | 1.0 |
| Summed Amount of Trans-Endo-Endo Isomer and Cis-Endo-Endo Isomer (Peak at Retention Time of Around 33.0 Minutes) | 10.0 | 16.7 | 57.8 | 97.3 |
| Summed Amount of Trans-Exo-Exo Isomer and Cis-Exo-Exo Isomer (Peak at Retention Time of Around 31.4 Minutes) | 0.9 | 0.2 | 0.7 | 0.3 |
| Summed Amount of Trans-Exo-Endo Isomer and Cis-Exo-Endo Isomer | 89.1 | 83.1 | 41.5 | 2.4 | flow rate of 3 L/min. Inside the inert oven, the coating film was cured by allowing the glass substrate to stand for 0.5 hours under a nitrogen atmosphere under a temperature condition of 25° C., and then heating for 0.5 hours under a temperature condition of 135° C., followed by further heating for 1 hour under a temperature condition of 300° C. (calcination temperature condition). Thereby, a film made of polyimide was formed on the glass substrate. Next, the thus obtained polyimide-coated glass was immersed in water of 90° C. for 0.5 hours to peel the polyimide film off of the glass substrate and collect the polyimide film. Thereby, a colorless and transparent film made of polyimide (polyimide film) was obtained. The film thickness of the polyimide film thus obtained was 13 μm.

Here, in order to identify the molecular structure of the compound forming the film thus obtained, an IR measuring apparatus (manufactured by JASCO Corporation under the trade name: FT/IR-4100) was used to measure the IR spectrum. The C=O stretching vibration of imidocarbonyl was observed at 1700 cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 2 presents the evaluation results of the characteristics of the polyimide thus obtained.

Comparative Example 3

First, a 30 ml three-necked flask was heated with a heat gun and sufficiently dried. Next, the atmospheric gas inside the sufficiently dried three-necked flask was substituted with nitrogen to fill the three-necked flask with a nitrogen atmosphere. Subsequently, after 2.1230 g (10 mmol) of m-tol was added into the three-necked flask, 16.336 g of N,N-dimethylacetamide was further added and stirred. Thereby, the aromatic diamine (m-tol) was dissolved into the N,N-dimethylacetamide to obtain a dissolution liquid.

Next, 1.9611 g (10 mmol) of 1,2,3,4-cyclobutane tetracarboxylic dianhydride (CBDA) as a tetracarboxylic dianhydride was added into the three-necked flask containing the dissolution liquid under a nitrogen atmosphere, followed by stirring for 12 hours under a nitrogen atmosphere at room temperature (25° C.). Thereby, a reaction liquid was obtained. Thus, a polyamic acid was formed in the reaction liquid. Note that, by using a portion of the reaction liquid (a solution of the polyamic acid), a dimethylacetamide solution having a polyamic acid concentration of 0.5 g/dL was prepared, and the intrinsic viscosity [η] of the polyamic acid, which was a reaction intermediate, was measured. The intrinsic viscosity [η] of the polyamic acid was 0.45 dL/g.

Next, the reaction liquid was spin-coated on a glass plate (length: 75 mm, width 50 mm, thickness 1.3 mm) to form a coating film on the glass plate. After that, the glass substrate having the coating film formed thereon was placed on a hot plate of 60° C. and was allowed to stand for 2 hours. Thereby, the solvent (dimethylacetamide) was vaporized and removed from the coating film. After the solvent removal treatment, the glass substrate having the coating film formed thereon was introduced into an inert oven in which nitrogen was flowing at a flow rate of 3 L/min. Inside the inert oven, the coating film was cured by allowing the glass substrate to stand for 0.5 hours under a nitrogen atmosphere under a temperature condition of 25° C., and then heating for 0.5 hours under a temperature condition of 135° C., followed by further heating for 1 hour under a temperature condition of 300° C. (calcination temperature condition). Thereby, a film made of polyimide was formed on the glass substrate. Next, the thus obtained polyimide-coated glass was immersed in water of 90° C. for 0.5 hours to peel the polyimide film off of the glass substrate and collect the polyimide film. Thereby, a colorless and transparent film made of polyimide (polyimide film) was obtained. The film thickness of the polyimide film thus obtained was 13 μm. Table 2 presents the evaluation results of the characteristics of the polyimide thus obtained.

TABLE 2

|  | Monomer | | Type of Solution | Polyimide Characteristics | | |
|---|---|---|---|---|---|---|
|  | Acid Dianhydride | Diamine | (Varnish) for Film Preparation | Total Luminous Transmittance (%) | Td5% (° C.) | Solubility |
| Example 3 | Product B (CpODA) | m-tol | Polyimide Solution (η: 0.43 dL/g) | 84.8 | 482 | C |
| Comparative Example 3 | CBDA | m-tol | Polyamic Acid Solution (η: 0.45 dL/g) | 87.9 | 460 | F |

Example 4

A colorless and transparent film made of polyimide (polyimide film) was obtained in the same manner as that of Example 3 except that 3.2024 g (10 mmol) of 2,2'-bis(trifluoromethyl)benzidine (TFMB) was used instead of using 2.1230 g (10 mmol) of m-tol as an aromatic diamine. The film thickness of the polyimide film thus obtained was 13 μm, and the intrinsic viscosity [r)] of the polyimide was 0.32 dL/g. Note that, when the IR spectrum was measured in the same manner as that of Example 3, the C=O stretching vibration of imidocarbonyl was observed at 1707 cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 3 presents the evaluation results of the characteristics of the polyimide thus obtained.

Example 5

A colorless and transparent film made of polyimide (polyimide film) was obtained in the same manner as that of Example 3 except that 3.2024 g (10 mmol) of 2,2'-bis(trifluoromethyl)benzidine (TFMB) was used instead of using 2.1230 g (10 mmol) of m-tol as an aromatic diamine and 3.8438 g (10 mmol) of the product C (isomeric mixture of CpODA obtained in Example 2) was used as a tetracarboxylic dianhydride. Note that the film thickness of the polyimide film thus obtained was 13 μm, and the intrinsic viscosity [η] of the polyamic acid obtained in the production was 0.40 dL/g. When IR analysis was carried out on the film made of polyimide thus obtained, the C=O stretching vibration of imidocarbonyl was observed at 1707 cm$^{-1}$, indicating that the film was indeed a film made of polyimide. In addition, it is apparent that, from the type of the tetracarboxylic dianhydride used (product C), the polyimide was a polyimide containing 83.1% by mole of the repeating units represented by the general formulae (6) and (7) relative to all repeating units and containing 69.4% by mole of the repeating unit represented by the general formula (6) relative to all repeating units. Table 3 presents the evaluation results of the characteristics of the polyimide thus obtained.

the polyimide film thus obtained was 13 μm, and the intrinsic viscosity [η] of the polyamic acid obtained in the production was 0.13 dL/g. Table 3 presents the evaluation results of the characteristics of the polyimide thus obtained.

TABLE 3

| | Monomer | | Type of Solution | Polyimide Characteristics | | |
| | | | | Total Luminous | | |
| | Acid Dianhydride | Diamine | (Varnish) for Film Preparation | Transmittance (%) | Td5% (° C.) | Solubility |
|---|---|---|---|---|---|---|
| Example 4 | Product B (CpODA) | TFMB | Polyimide Solution (η: 0.32 dL/g) | 90.0 | 493 | A |
| Example 5 | Product C (CpODA) | TFMB | Polyimide Solution (η: 0.40 dL/g) | 88.8 | 491 | A |
| Comparative Example 4 | Product D (CpODA) | TFMB | Polyamic Acid Solution (η: 0.37 dL/g) | 90.8 | 484 | D |
| Comparative Example 5 | CBDA | TFMB | Polyamic Acid Solution (η: 0.13 dL/g) | 89.8 | 437 | F |

Comparative Example 4

A colorless and transparent film made of polyimide (polyimide film) was obtained in the same manner as that of Comparative Example 3 except that 3.2024 g (10 mmol) of TFMB was used instead of using 2.1230 g (10 mmol) of m-tol as an aromatic diamine and 3.8438 g (10 mmol) of the product D (isomeric mixture of CpODA obtained in Comparative Example 1) was used instead of using 1.9611 g (10 mmol) of CBDA as a tetracarboxylic dianhydride. Note that the film thickness of the polyimide film thus obtained was 13 μm, and the intrinsic viscosity [η] of the polyamic acid obtained in the production was 0.37 dL/g. In addition, it is apparent that, from the type of the tetracarboxylic dianhydride used (product D), the polyimide was a polyimide containing 41.5% by mole of the repeating units represented by the general formulae (6) and (7) relative to all repeating units and containing 25.2% by mole of the repeating unit represented by the general formula (6) relative to all repeating units. Table 3 presents the evaluation results of the characteristics of the polyimide thus obtained.

Comparative Example 5

A colorless and transparent film made of polyimide (polyimide film) was obtained in the same manner as that of Comparative Example 3 except that 3.2024 g (10 mmol) of TFMB was used instead of using 2.1230 g (10 mmol) of m-tol as an aromatic diamine. Note that the film thickness of Example 6

A colorless and transparent film made of polyimide (polyimide film) was obtained in the same manner as that of Example 3 except that 2.9234 g (10 mmol) of 1,3-bis(4-aminophenoxy)benzene (TPE-R) was used instead of using 2.1230 g (10 mmol) of m-tol as an aromatic diamine. The film thickness of the polyimide film thus obtained was 13 μm, and the intrinsic viscosity [η] of the polyimide was 0.43 dL/g. Note that, when the IR spectrum was measured in the same manner as that of Example 3, the C=O stretching vibration of imidocarbonyl was observed at 1703 cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 4 presents the evaluation results of the characteristics of the polyimide thus obtained.

Comparative Example 6

A colorless and transparent film made of polyimide (polyimide film) was obtained in the same manner as that of Comparative Example 3 except that 2.9234 g (10 mmol) of TPE-R was used instead of using 2.1230 g (10 mmol) of m-tol as an aromatic diamine and 3.8438 g (10 mmol) of the product D (isomeric mixture of CpODA obtained in Comparative Example 1) was used instead of using 1.9611 g (10 mmol) of CBDA as a tetracarboxylic dianhydride. Note that the film thickness of the polyimide film thus obtained was 13 μm, and the intrinsic viscosity [η] of the polyamic acid obtained in the production was 0.50 dL/g. In addition, it is apparent that, from the type of the tetracarboxylic dianhydride used (product D), the polyimide was a polyimide containing 41.5% by mole of the repeating units represented by the general formulae (6) and (7) relative to all repeating units and containing 25.2% by mole of the repeating unit represented by the general formula (6) relative to all repeating units. Table 4 presents the evaluation results of the characteristics of the polyimide thus obtained.

Comparative Example 7

A colorless and transparent film made of polyimide (polyimide film) was obtained in the same manner as that of Comparative Example 3 except that 2.9234 g (10 mmol) of TPE-R was used instead of using 2.1230 g (10 mmol) of m-tol as an aromatic diamine. Note that the film thickness of the polyimide film thus obtained was 13 μm, and the intrinsic viscosity [η] of the polyamic acid obtained in the production was 0.25 dL/g. Table 4 presents the evaluation results of the characteristics of the polyimide thus obtained.

Comparative Example 8

A colorless and transparent film made of polyimide (polyimide film) was obtained in the same manner as that of Comparative Example 3 except that 2.9234 g (10 mmol) of APB-N was used instead of using 2.1230 g (2.1230 mmol) of m-tol as an aromatic diamine and 3.8438 g (10 mmol) of the product D (isomeric mixture of CpODA obtained in Comparative Example 1) was used instead of using 1.9611 g (10 mmol) of CBDA as a tetracarboxylic dianhydride. Note that the film thickness of the polyimide film thus obtained was 13 μm, and the intrinsic viscosity [η] of the polyamic acid obtained in the production was 0.34 dL/g. In addition, it is apparent that, from the type of the tetracarboxylic dianhydride used (product D), the polyimide was a polyimide containing 41.5% by mole of the repeating units represented by the general formulae (6) and (7) relative to all repeating units and containing 25.2% by mole of the repeating unit represented by the general formula (6) relative to all repeating units. Table 5 presents the evaluation results of the characteristics of the polyimide thus obtained.

TABLE 4

| | Monomer | | Type of Solution | Polyimide Characteristics | | |
|---|---|---|---|---|---|---|
| | Acid Dianhydride | Diamine | (Varnish) for Film Preparation | Total Luminous Transmittance (%) | Td5% (° C.) | Solubility |
| Example 6 | Product B (CpODA) | TPE-R | Polyimide Solution (η: 0.43 dL/g) | 88.2 | 496 | C |
| Comparative Example 6 | Product D (CpODA) | TPE-R | Polyamic Acid Solution (η: 0.50 dL/g) | 88.3 | 474 | D |
| Comparative Example 7 | CBDA | TPE-R | Polyamic Acid Solution (η: 0.25 dL/g) | 87.9 | 439 | F |

Example 7

A colorless and transparent film made of polyimide (polyimide film) was obtained in the same manner as that of Example 3 except that 2.9234 g (10 mmol) of 1,3-bis(3-aminophenoxy)benzene (APB-N) was used instead of using 2.1230 g (10 mmol) of m-tol as an aromatic diamine. The film thickness of the polyimide film thus obtained was 13 μm, and the intrinsic viscosity [r] of the polyimide was 0.27 dL/g. Note that, when the IR spectrum was measured in the same manner as that of Example 3, the C=O stretching vibration of imidocarbonyl was observed at 1704 cm$^{-1}$ cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 5 presents the evaluation results of the characteristics of the polyimide thus obtained.

TABLE 5

| | Monomer | | Type of Solution | Polyimide Characteristics | | |
|---|---|---|---|---|---|---|
| | Acid Dianhydride | Diamine | (Varnish) for Film Preparation | Total Luminous Transmittance (%) | Td5% (° C.) | Solubility |
| Example 7 | Product B (CpODA) | APB-N | Polyimide Solution (η: 0.27 dL/g) | 86.6 | 494 | C |
| Comparative Example 8 | Product D (CpODA) | APB-N | Polyamic Acid Solution (η: 0.34 dL/g) | 85.0 | 487 | D |

Example 8

A colorless and transparent film made of polyimide (polyimide film) was obtained in the same manner as that of Example 3 except that 2.0024 g (10 mmol) of 4,4'-diaminodiphenyl ether (DDE) was used instead of using 2.1230 g (10 mmol) of m-tol as an aromatic diamine. The film thickness of the polyimide film thus obtained was 13 μm, and the intrinsic viscosity [η] of the polyimide was 0.42 dL/g. Note that, when the IR spectrum was measured in the same manner as that of Example 3, the C=O stretching vibration of imidocarbonyl was observed at 1700 cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 6 presents the evaluation results of the characteristics of the polyimide thus obtained.

Example 9

First, a 30 ml three-necked flask was heated with a heat gun and sufficiently dried. Next, the atmospheric gas inside the sufficiently dried three-necked flask was substituted with nitrogen to fill the three-necked flask with a nitrogen atmosphere. Subsequently, after 2.0024 g (10 mmol) of DDE was added into the three-necked flask, 23.385 g of N,N-dimethylacetamide was further added and stirred. Thereby, the aromatic diamine (DDE) was dissolved into the N,N-dimethylacetamide to obtain a dissolution liquid.

Next, 3.8438 g (10 mmol) of the product B (isomeric mixture of CpODA obtained in Example 1) as a tetracarboxylic dianhydride was added into the three-necked flask containing the dissolution liquid under a nitrogen atmosphere, followed by stirring for 12 hours under a nitrogen atmosphere at room temperature (25° C.). Thereby, a reaction liquid was obtained. Thus, a polyamic acid was formed in the reaction liquid. Note that, by using a portion of the reaction liquid (a solution of the polyamic acid), a dimethylacetamide solution having a polyamic acid concentration of 0.5 g/dL was prepared, and the intrinsic viscosity [η] of the polyamic acid, which was a reaction intermediate, was measured. The intrinsic viscosity [η] of the polyamic acid was 0.59 dL/g. Note that it is apparent that, from the type of the tetracarboxylic dianhydride used (product B), the polyamic acid was a polyamic acid containing 89.1% by mole of the repeating units represented by the general formulae (4) and (5) in which both of X are hydrogen atoms relative to all repeating units and containing 60.4% by mole of the repeating unit represented by the general formula (4) relative to all repeating units.

Next, the reaction liquid was spin-coated on a glass plate (length: 75 mm, width 50 mm, thickness 1.3 mm) to form a coating film on the glass plate. After that, the glass substrate having the coating film formed thereon was placed on a hot plate of 60° C. and was allowed to stand for 2 hours. Thereby, the solvent (dimethylacetamide) was vaporized and removed from the coating film. After the solvent removal treatment, the glass substrate having the coating film formed thereon was introduced into an inert oven in which nitrogen was flowing at a flow rate of 3 L/min. Inside the inert oven, the coating film was cured by allowing the glass substrate to stand for 0.5 hours under a nitrogen atmosphere under a temperature condition of 25° C., and then heating for 0.5 hours under a temperature condition of 135° C., followed by further heating for 1 hour under a temperature condition of 300° C. (calcination temperature condition). Thereby, a film made of polyimide was formed on the glass substrate. Next, the thus obtained polyimide-coated glass was immersed in water of 90° C. for 0.5 hours to peel the polyimide film off of the glass substrate and collect the polyimide film. Thereby, a colorless and transparent film made of polyimide (polyimide film) was obtained. The film thickness of the polyimide film thus obtained was 13 μm.

When IR analysis was carried out on the film made of polyimide thus obtained, the C=O stretching vibration of imidocarbonyl was observed at 1700 cm$^{-1}$, indicating that the film was a film made of polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 6 presents the evaluation results of the characteristics of the polyimide thus obtained.

Comparative Example 9

A colorless and transparent film made of polyimide (polyimide film) was obtained in the same manner as that of Comparative Example 3 except that 2.0024 g (10 mmol) of DDE was used instead of using 2.1230 g (10 mmol) of m-tol as an aromatic diamine and 3.8438 g (10 mmol) of the product D (isomeric mixture of CpODA obtained in Comparative Example 1) was used instead of using 1.9611 g (10 mmol) of CBDA as a tetracarboxylic dianhydride. Note that the film thickness of the polyimide film thus obtained was 13 μm, and the intrinsic viscosity [η] of the polyamic acid obtained in the production was 0.72 dL/g. In addition, it is apparent that, from the type of the tetracarboxylic dianhydride used (product D), the polyimide was a polyimide containing 41.5% by mole of the repeating units represented by the general formulae (6) and (7) relative to all repeating units and containing 25.2% by mole of the repeating unit represented by the general formula (6) relative to all repeating units. Table 6 presents the evaluation results of the characteristics of the polyimide thus obtained.

TABLE 6

| | Monomer | | Type of Solution | Polyimide Characteristics | | |
| --- | --- | --- | --- | --- | --- | --- |
| | Acid Dianhydride | Diamine | (Varnish) for Film Preparation | Total Luminous Transmittance (%) | Td5% (° C.) | Solubility |
| Example 8 | Product B (CpODA) | DDE | Polyimide Solution (η: 0.42 dL/g) | 87.9 | 493 | C |
| Example 9 | Product B (CpODA) | DDE | Polyamic Acid Solution (η: 0.59 dL/g) | 88.1 | 480 | C |
| Comparative Example 9 | Product D (CpODA) | DDE | Polyamic Acid Solution (η: 0.72 dL/g) | 89.7 | 483 | D |

Example 10

A colorless and transparent film made of polyimide (polyimide film) was obtained in the same manner as that of Example 3 except that 4.3249 g (10 mmol) of bis[4-(4-aminophenoxy)phenyl]sulfone (BAPS) was used instead of using 2.1230 g (10 mmol) of m-tol as an aromatic diamine.

The film thickness of the polyimide film thus obtained was 13 μm, and the intrinsic viscosity [η] of the polyimide was 0.47 dL/g. Note that, when the IR spectrum was measured in the same manner as that of Example 3, the C=O stretching vibration of imidocarbonyl was observed at 1704 cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 7 presents the evaluation results of the characteristics of the polyimide thus obtained.

Comparative Example 10

A colorless and transparent film made of polyimide (polyimide film) was obtained in the same manner as that of Comparative Example 3 except that 4.3249 g (10 mmol) of BAPS was used instead of using 2.1230 g (10 mmol) of m-tol as an aromatic diamine and 3.8438 g (10 mmol) of the product D (isomeric mixture of CpODA obtained in Comparative Example 1) was used instead of using 1.9611 g (10 mmol) of CBDA as a tetracarboxylic dianhydride. Note that the film thickness of the polyimide film thus obtained was 13 μm, and the intrinsic viscosity [r] of the polyamic acid obtained in the production was 0.75 dL/g. In addition, it is apparent that, from the type of the tetracarboxylic dianhydride used (product D), the polyimide was a polyimide containing 41.5% by mole of the repeating units represented by the general formulae (6) and (7) relative to all repeating units and containing 25.2% by mole of the repeating unit represented by the general formula (6) relative to all repeating units. Table 7 presents the evaluation results of the characteristics of the polyimide thus obtained.

aminophenoxy)phenyl]sulfone (BAPS-M) was used instead of using 2.1230 g (10 mmol) of m-tol as an aromatic diamine. The film thickness of the polyimide film thus obtained was 13 μm, and the intrinsic viscosity [r] of the polyimide was 0.28 dL/g. Note that, when the IR spectrum was measured in the same manner as that of Example 3, the C=O stretching vibration of imidocarbonyl was observed at 1705 cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 8 presents the evaluation results of the characteristics of the polyimide thus obtained.

Comparative Example 11

A colorless and transparent film made of polyimide (polyimide film) was obtained in the same manner as that of Comparative Example 3 except that 4.3249 g (10 mmol) of BAPS-M was used instead of using 2.1230 g (10 mmol) of m-tol as an aromatic diamine and 3.8438 g (10 mmol) of the product D (isomeric mixture of CpODA obtained in Comparative Example 1) was used instead of using 1.9611 g (10 mmol) of CBDA as a tetracarboxylic dianhydride. Note that the film thickness of the polyimide film thus obtained was 13 μm, and the intrinsic viscosity [η] of the polyamic acid obtained in the production was 0.22 dL/g. In addition, it is apparent that, from the type of the tetracarboxylic dianhydride used (product D), the polyimide was a polyimide containing 41.5% by mole of the repeating units represented

TABLE 7

| | Monomer | | | Polyimide Characteristics | | |
| | Acid Dianhydride | Diamine | Type of Solution (Varnish) for Film Preparation | Total Luminous Transmittance (%) | Td5% (° C.) | Solubility |
| --- | --- | --- | --- | --- | --- | --- |
| Example 10 | Product B (CpODA) | BAPS | Polyimide Solution (η: 0.47 dL/g) | 83.4 | 495 | C |
| Comparative Example 10 | Product D (CpODA) | BAPS | Polyamic Acid Solution (η: 0.75 dL/g) | 87.0 | 479 | D |

Example 11

A colorless and transparent film made of polyimide (polyimide film) was obtained in the same manner as that of Example 3 except that 4.3249 g (10 mmol) of bis[4-(3- by the general formulae (6) and (7) relative to all repeating units and containing 25.2% by mole of the repeating unit represented by the general formula (6) relative to all repeating units. Table 8 presents the evaluation results of the characteristics of the polyimide thus obtained.

TABLE 8

| | Monomer | | | Polyimide Characteristics | | |
| | Acid Dianhydride | Diamine | Type of Solution (Varnish) for Film Preparation | Total Luminous Transmittance (%) | Td5% (° C.) | Solubility |
| --- | --- | --- | --- | --- | --- | --- |
| Example 11 | Product B (CpODA) | BAPS-M | Polyimide Solution (η: 0.28 dL/g) | 85.4 | 494 | B |
| Comparative Example 11 | Product D (CpODA) | BAPS-M | Polyamic Acid Solution (η: 0.22 dL/g) | 89.6 | 463 | D |

Example 12

A colorless and transparent film made of polyimide (polyimide film) was obtained in the same manner as that of Example 3 except that 4.1052 g (10 mmol) of 2,2-bis[4-(4-aminophenoxy)phenyl]propane (BAPP) was used instead of using 2.1230 g (10 mmol) of m-tol as an aromatic diamine. The film thickness of the polyimide film thus obtained was 13 μm, and the intrinsic viscosity [η] of the polyimide was 0.46 dL/g. Note that, when the IR spectrum was measured in the same manner as that of Example 3, the C=O stretching vibration of imidocarbonyl was observed at 1705 cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 9 presents the evaluation results of the characteristics of the polyimide thus obtained.

Comparative Example 12

A colorless and transparent film made of polyimide (polyimide film) was obtained in the same manner as that of Comparative Example 3 except that 4.1052 g (10 mmol) of BAPP was used instead of using 2.1230 g (10 mmol) of m-tol as an aromatic diamine and 3.8438 g (10 mmol) of the product D (isomeric mixture of CpODA obtained in Comparative Example 1) was used instead of using 1.9611 g (10 mmol) of CBDA as a tetracarboxylic dianhydride. Note that the film thickness of the polyimide film thus obtained was 13 μm, and the intrinsic viscosity [η] of the polyamic acid obtained in the production was 0.71 dL/g. In addition, it is apparent that, from the type of the tetracarboxylic dianhydride used (product D), the polyimide was a polyimide containing 41.5% by mole of the repeating units represented by the general formulae (6) and (7) relative to all repeating units and containing 25.2% by mole of the repeating unit represented by the general formula (6) relative to all repeating units. Table 9 presents the evaluation results of the characteristics of the polyimide thus obtained.

Comparative Example 13

A colorless and transparent film made of polyimide (polyimide film) was obtained in the same manner as that of Comparative Example 3 except that 4.1052 g (10 mmol) of BAPP was used instead of using 2.1230 g (10 mmol) of m-tol as an aromatic diamine and 3.8438 g (10 mmol) of the product E (isomeric mixture of CpODA obtained in Comparative Example 2) was used instead of using 1.9611 g (10 mmol) of CBDA as a tetracarboxylic dianhydride. Note that the film thickness of the polyimide film thus obtained was 13 μm, and the intrinsic viscosity [η] of the polyamic acid obtained in the production was 0.51 dL/g. In addition, it is apparent that, from the type of the tetracarboxylic dianhydride used (product E), the polyimide was a polyimide containing 2.4% by mole of the repeating units represented by the general formulae (6) and (7) relative to all repeating units and containing 1.4% by mole of the repeating unit represented by the general formula (6) relative to all repeating units. Table 9 presents the evaluation results of the characteristics of the polyimide thus obtained.

TABLE 9

| | Monomer | | Type of Solution | Polyimide Characteristics | | |
| --- | --- | --- | --- | --- | --- | --- |
| | Acid Dianhydride | Diamine | (Varnish) for Film Preparation | Total Luminous Transmittance (%) | Td5% (° C.) | Solubility |
| Example 12 | Product B (CpODA) | BAPP | Polyimide Solution (η: 0.46 dL/g) | 85.2 | 496 | A |
| Comparative Example 12 | Product D (CpODA) | BAPP | Polyamic Acid Solution (η: 0.71 dL/g) | 89.0 | 483 | C |
| Comparative Example 13 | Product E (CpODA) | BAPP | Polyamic Acid Solution (η: 0.51 dL/g) | 87.8 | 490 | D |

Example 13

A colorless and transparent film made of polyimide (polyimide film) was obtained in the same manner as that of Example 3 except that 3.4845 g (10 mmol) of 9,9-bis(4-aminophenyl) fluorene (FDA) was used instead of using 2.1230 g (10 mmol) of m-tol as an aromatic diamine. The film thickness of the polyimide film thus obtained was 13 μm, and the intrinsic viscosity [r)] of the polyimide was 0.31 dL/g. Note that, when the IR spectrum was measured in the same manner as that of Example 3, the C=O stretching vibration of imidocarbonyl was observed at 1705 cm$^{-1}$, indicating that the compound constituting the obtained film was a polyimide. In addition, it is apparent that, from the type of the tetracarboxylic dianhydride used (product B), the polyimide was a polyimide containing 89.1% by mole of the repeating units represented by the general formulae (6) and (7) relative to all repeating units and containing 60.4% by mole of the repeating unit represented by the general formula (6) relative to all repeating units. Table 10 presents the evaluation results of the characteristics of the polyimide thus obtained.

TABLE 10

| | Monomer | | Type of Solution | Polyimide Characteristics | | |
| --- | --- | --- | --- | --- | --- | --- |
| | Acid Dianhydride | Diamine | (Varnish) for Film Preparation | Total Luminous Transmittance (%) | Td5% (° C.) | Solubility |
| Example 13 | Product B (CpODA) | FDA | Polyimide Solution (η: 0.31 dL/g) | 86.7 | 502 | C |

[On Characteristics of Polyimide]

As is apparent from the results presented in Tables 1 to 9, the comparison of polyimides having the same type of aromatic diamine reveals that the solubility to a solvent is higher in the case of forming a polyimide by use of the tetracarboxylic dianhydride of the present invention (Examples 1 and 2). In addition, the results presented in Tables 3 to 9 reveals that the polyimide of the present invention is also higher in solubility than the polyimide obtained using CpODA (product D) obtained in Comparative Example 1 or CpODA (product E) obtained in Comparative Example 2 having different isomer ratios as tetracarboxylic acids. Specifically, the results presented in Tables 3 to 9 reveals that, in the case of using the tetracarboxylic dianhydride of the present invention composed of CpODA satisfying the conditions that the summed amount of the trans-exo-endo isomer and the cis-exo-endo isomer is 50% by mole or more and the content of the trans-exo-endo isomer is 30% by mole or more relative to the total amount of the stereoisomers (Examples 1 and 2), the solubility of the obtained polyimide is higher, and the solubility of the finally obtained polyimide can be further improved by using a tetracarboxylic dianhydride satisfying the above conditions, as compared with the case of using a tetracarboxylic dianhydride composed of CpODA not satisfying the above conditions (Comparative Examples 1 and 2). In addition, as is apparent from the results presented in Tables 1 to 10, it is revealed from the values of total luminous transmittance and the values of Td5% that the obtained polyimide (polyimide of the present invention) has sufficiently high levels of transparency and heat resistance in the case of forming a polyimide using the tetracarboxylic dianhydride of the present invention (Examples 1 and 2).

INDUSTRIAL APPLICABILITY

As has been described above, the present invention makes it possible to provide a tetracarboxylic dianhydride which can be preferably used for producing a polyimide having higher solubility while having sufficiently high levels of heat resistance and transparency. In addition, the present invention makes it possible to provide a polyimide which can have higher solubility while having sufficiently high levels of heat resistance and transparency, and a polyimide solution containing the polyimide. Moreover, the present invention makes it possible to provide a polyimide precursor resin which can be preferably used for producing the polyimide, and a polyimide precursor resin solution containing the polyimide precursor resin. Such a polyimide is excellent in solubility, and thus is high in processability and can be preferably used for various applications.

The invention claimed is:

1. A tetracarboxylic dianhydride represented by the following general formula (1):

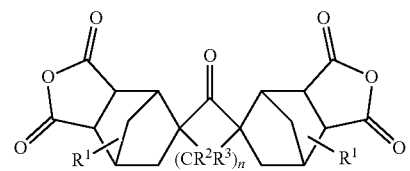

wherein in the formula (1), $R^1$, $R^2$, and $R^3$ each independently represent one selected from the group consisting of a hydrogen atom, alkyl groups having 1 to 10 carbon atoms, and a fluorine atom, and n represents an integer of 0 to 12, wherein a summed amount of a stereoisomer (A) represented by the following general formula (2):

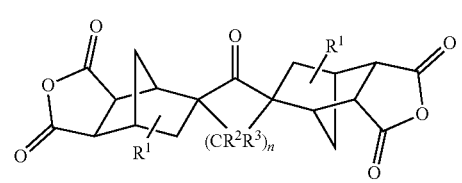

wherein $R^1$, $R^2$, $R^3$, and n in the formula (2) have the same definitions as those of $R^1$, $R^2$, $R^3$, and n in the general formula (1), respectively and a stereoisomer (B) represented by the following general formula (3):

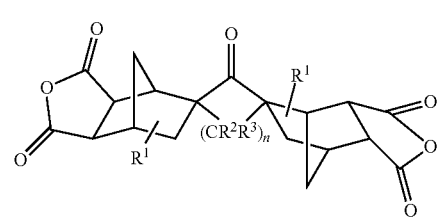

wherein $R^1$, $R^2$, $R^3$, and n in the formula (3) have the same definitions as those of $R^1$, $R^2$, $R^3$, and n in the general formula (1), respectively, is 80% by mole or more relative to a total amount of stereoisomers based on three-dimensional configurations of two norbornane rings in the general formula (1), wherein a content of the stereoisomer (A) is 60% to 80% by mole relative to the total amount of the stereoisomers, and wherein a content of the stereoisomer (B) is 10% to 40% by mole relative to the total amount of the stereoisomers.

2. A polyimide precursor resin, wherein
a summed amount of
  a repeating unit (A') represented by the following general formula (4):

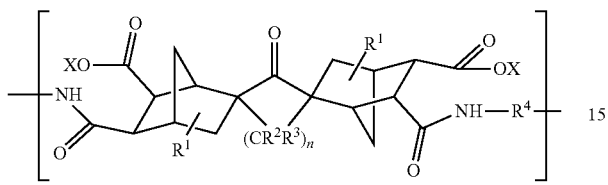

(4)

wherein in the formula (4), $R^1$, $R^2$, and $R^3$ each independently represent one selected from the group consisting of a hydrogen atom, alkyl groups having 1 to 10 carbon atoms, and a fluorine atom, n represents an integer of 0 to 12, $R^4$ represents an arylene group having 6 to 50 carbon atoms, and X each independently represent one selected from the group consisting of a hydrogen atom, alkyl groups having 1 to 6 carbon atoms, and alkyl silyl groups having 3 to 9 carbon atoms and
a repeating unit (B') represented by the following general formula (5):

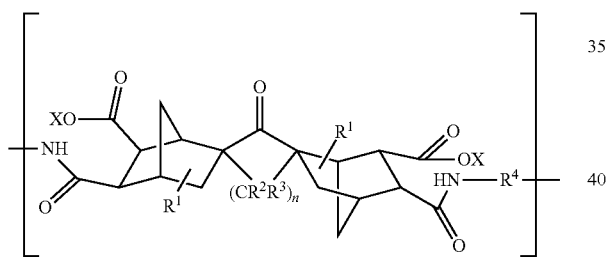

(5)

wherein $R^1$, $R^2$, $R^3$, $R^4$, n, and X in the formula (5) have the same definitions as those of $R^1$, $R^2$, $R^3$, $R^4$, n, and X in the general formula (4), respectively,
is 80% by mole or more relative to a total amount of all repeating units,
a content of the repeating unit (A') is 60% to 80% by mole relative to the total amount of all the repeating units, and
a content of the repeating unit (B') is 10% to 40% by mole relative to the total amount of all the repeating units.

3. A polyimide, wherein
a summed amount of
  a repeating unit (A) represented by the following general formula (6):

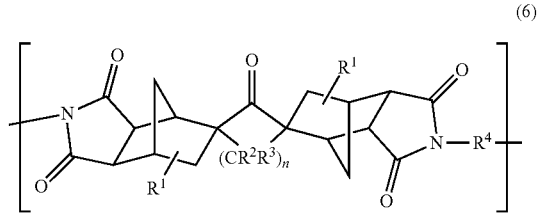

(6)

wherein in the formula (6), $R^1$, $R^2$, and $R^3$ each independently represent one selected from the group consisting of a hydrogen atom, alkyl groups having 1 to 10 carbon atoms, and a fluorine atom, n represents an integer of 0 to 12, and $R^4$ represents an arylene group having 6 to 50 carbon atoms and
a repeating unit (B) represented by the following general formula (7):

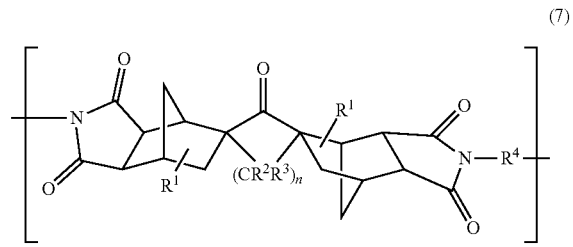

(7)

wherein $R^1$, $R^2$, $R^3$, $R^4$, and n in the formula (7) have the same definitions as those of $R^1$, $R^2$, $R^3$, $R^4$, and n in the general formula (6), respectively,
is 80% by mole or more relative to a total amount of all repeating units,
a content of the repeating unit (A) is 60% to 80% by mole relative to the total amount of all the repeating units, and
a content of the repeating unit (B) is 10% to 40% by mole relative to the total amount of all the repeating units.

4. A polyimide solution comprising the polyimide according to claim 3 and an organic solvent.

5. A polyimide precursor resin solution comprising the polyimide precursor resin according to claim 2 and an organic solvent.

* * * * *